United States Patent
Chandraratna

Patent Number: 5,089,509
Date of Patent: Feb. 18, 1992

[54] DISUBSTITUTED ACETYLENES BEARING HETEROAROMATIC AND HETEROBICYCLIC GROUPS HAVING RETINOID LIKE ACTIVITY

[75] Inventor: Roshantha A. S. Chandraratna, El Toro, Calif.

[73] Assignee: Allergan, Inc., Irvine, Calif.

[21] Appl. No.: 326,191

[22] Filed: Mar. 20, 1989

Related U.S. Application Data

[63] Continuation-in-part of Ser. No. 246,037, Sep. 15, 1988, abandoned.

[51] Int. Cl.⁵ .................. A61K 31/335; A61K 31/38; C07D 413/06; C07D 413/12
[52] U.S. Cl. .................. 514/337; 514/247; 514/269; 514/255; 514/432; 514/444; 514/456; 514/461; 514/863; 544/238; 544/333; 544/376; 549/13; 549/23; 549/60; 549/398; 549/425; 549/426; 549/427; 546/269; 546/274
[58] Field of Search ............. 546/269, 274; 514/337, 514/863

[56] References Cited

U.S. PATENT DOCUMENTS

| | | | |
|---|---|---|---|
| 4,307,108 | 12/1981 | Belletire et al. | 546/269 |
| 4,739,098 | 4/1988 | Chandraratna | 580/8 |
| 4,810,804 | 3/1989 | Chandraratna | 514/311 |
| 4,895,868 | 1/1990 | Chandraratna | 514/432 |

FOREIGN PATENT DOCUMENTS 133795 1/1985 European Pat. Off.
176034 4/1986 European Pat. Off.

OTHER PUBLICATIONS

*J. Med. Chem.*, 1987, vol. 30, No. 8, pp. 1474–1482, Spruce et al.
*J. Med. Chem.*, 1984, vol. 27, pp. 1516–1531, Dawson et al.

Primary Examiner—Johann Richter
Attorney, Agent, or Firm—Gabor L. Szekeres; Martin A. Voet; Robert J. Baran

[57] ABSTRACT

Retinoid-like activity is exhibited by compounds of the formula

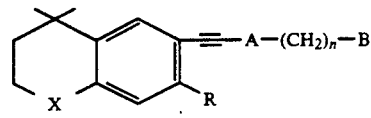

where X is S, O, or NR' where R' is hydrogen or lower alkyl; R is hydrogen or lower alkyl; A is pyridyl, thienyl, furyl, pyridazinyl, pyrimidinyl or pyrazinyl; n is 0–2; and B is H, —COOH or a pharmaceutically acceptable salt, ester or amide thereof, —CH$_2$OH or an ether or ester derivative, or —CHO or an acetal derivative, or —COR$_1$ or a ketal derivative where R$_1$ is —(CH$_2$)$_m$CH$_3$ where m is 0–4, or a pharmaceutically acceptable salt thereof.

19 Claims, No Drawings

DISUBSTITUTED ACETYLENES BEARING HETEROAROMATIC AND HETEROBICYCLIC GROUPS HAVING RETINOID LIKE ACTIVITY

This is a continuation-in-part of pending U.S. application Ser. No. 07/246,037 filed Sept. 15, 1988 now abandoned.

BACKGROUND

This invention relates to novel compounds having retinoid-like activity. More specifically, the invention relates to compounds having an ethynylheteroaromatic acid portion and a second portion which is a tetrahydroquinolinyl, thiocromanyl, or chromanyl group. The acid function may also be converted to an alcohol, aldehyde or ketone or derivatives thereof, or may be reduced to —CH$_3$.

RELATED ART

Carboxylic acid derivatives useful for inhibiting the degeneration of cartilage of the general formula 4-(2-(4,4-dimethyl-6-X)-2-methylvinyl)benzoic acid where X is tetrahydroquinolinyl, chromanyl or thiochromanyl are disclosed in European Patent Application 0133795 published Jan. 9, 1985. See also European Patent Application 176034A published Apr. 2, 1986 where tetrahydronaphthalene compounds having an ethynylbenzoic acid group are disclosed.

SUMMARY OF THE INVENTION

This invention covers compounds of formula I

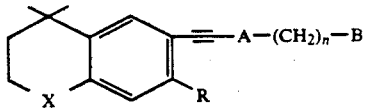

wherein X is S, O, or NR' where R' is hydrogen or lower alkyl; R is hydrogen or lower alkyl; A is pyridinyl, thienyl, furyl, pyridazinyl, pyrimidinyl or pyrazinyl; n is 0-2; and B is H, —COOH or a pharmaceutically acceptable salt, ester or amide thereof, —CH$_2$OH or an ether or ester derivative, or —CHO or an acetal derivative, or —COR$_1$ or a ketal derivative where R$_1$ is —(CH$_2$)$_m$CH$_3$ where m is 0-4.

In a second aspect, this invention relates to the use of the compounds of formula I for treating dermatoses, such as acne, Darier's disease, psoriasis, icthyosis, eczema, atopic dermatitis and epithelial cancers. These compounds are also useful in the treatment of arthritic diseases and other immunological disorders (e.g., lupus erythematosus), in promoting wound healing, in treating dry eye syndrome and in reversing the effects of sun damage to skin.

This invention also relates to a pharmaceutical formulation comprising a compound of formula I in admixture with a pharmaceutically acceptable excipient.

In another aspect, this invention relates to the process for making a compound of formula I which process comprises reacting a compound of formula II with a compound of formula III in the presence of cuprous iodide and Pd(PQ$_3$)$_2$Cl$_2$ or a similar complex where the two formulas are represented by graphics II and III

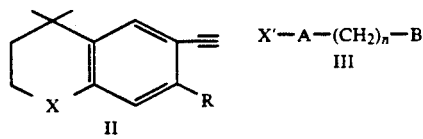

where X' is a halogen, preferably I; n and A are the same as defined above; and B is H, or a protected acid, alcohol, aldehyde or ketone, giving the corresponding compound of formula I; or to the process of making a compound of formula I which consists of reacting a zinc salt of formula IV with a compound of formula III in the presence of Pd(PQ$_3$)$_4$ (Q is phenyl) or a similar complex,

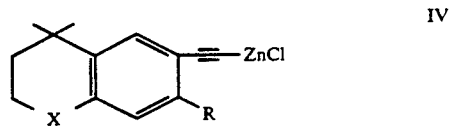

giving the corresponding compound of formula I; or homologating a compound of the formula

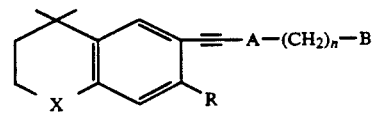

where
n is 0-1 to give an acid of formula I; or
converting an acid of formula I to a salt; or
forming an acid addition salt;
converting an acid of formula I to an ester; or
converting an acid of formula I to an amide; or
reducing an acid of formula I to an alcohol or aldehyde; or
converting an alcohol of formula I to an ether or ester; or
oxidizing an alcohol of formula I to an aldehyde; or
converting an aldehyde of formula I to an acetal; or
converting a ketone of formula I to a ketal.

GENERAL EMBODIMENTS

Definitions

The term "ester" as used here refers to and covers any compound falling within the definition of that term as classically used in organic chemistry. Where A is —COOH, this term covers the products derived from treatment of this function with alcohols. Where the ester is derived from compounds where A is —CH$_2$OH, this term covers compounds of the formula —CH$_2$OOCR where R is any substituted or unsubstituted aliphatic, aromatic or aliphatic-aromatic group.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Here, and where ever else used, lower alkyl means having 1-6 carbon atoms. Also preferred are the phenyl or lower alkylphenyl esters.

Amide has the meaning classically accorded that term in organic chemistry. In this instance it includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals includes the radicals of the formula —CK where K is (—OR)$_2$. Here, R is lower alkyl. Also, K may be —OR$_1$O— where R$_1$ is lower alkyl of 2–5 carbon atoms, straight chain or branched.

A pharmaceutically acceptable salt may be prepared for any compound of this invention having a functionality capable of forming such salt, for example an acid amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as a mono-, di- or tri-acid may also be used.

The preferred compounds of this invention are those where the ethynyl group and the B group are attached to the 2 and 5 positions respectively of a pyridine ring (the 6 and 3 positions in the nicotinic acid nomenclature being equivalent to the 2/5 designation in the pyridine nomenclature) or the 5 and 2 positions respectively of a thiophene group respectively; n is 0; and B is —COOH, an alkali metal salt or organic amine salt, or a lower alkyl ester, or —CH$_2$OH and the lower alkyl esters and ethers thereof, or —CHO and acetal derivatives thereof.

The most preferred compounds are:
ethyl 6-(2-(4,4-dimethylthiochroman-6-yl)ethynyl)-nicotinate;
6-(2-(4,4-dimethylthiochroman-6-yl)ethynyl)nicotinic acid;
6-(2-(4,4-dimethylchroman-6-yl)ethynyl)nicotinic acid;
ethyl 6-(2-(4,4-dimethylchroman-6-yl)ethynyl)nicotinate;
ethyl 6-(2-(4,4,7-trimethylthiochroman-6-yl)-ethynyl)-nicotinate;
ethyl 6-(2-(4,4-dimethyl-1,2,3,4-tetrahydroquinolin-6-yl)ethynyl)nicotinate;
ethyl 5-(2-(4,4-dimethylthiochroman-6-yl)ethynyl)thiophene-2-carboxylate.
6-(2-(4,4-dimethylthiochroman-6-yl)-ethynyl)-3-pyridylmethanol; and
2-(2-(4,4-dimethylthiochroman-6-yl)-ethynyl)-5-pyridinecarboxaldehyde.

The compounds of this invention may be administered systemically or topically, depending on such considerations as the condition to be treated, need for site-specific treatment, quantity of drug to be administered, and similar considerations.

In the treatment of dermatoses, it will generally be preferred to administer the drug topically, though in certain cases such as treatment of severe cystic acne, oral administration may also be used. Any common topical formulation such as a solution, suspension, gel, ointment, or salve and the like may be used. Preparation of such topical formulations are well described in the art of pharmaceutical formulations as exemplified, for example, *Remington's Pharmaceutical Science*, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation containing between 0.001 and 5 percent by weight, preferably about 0.01 to 1%, will usually constitute a therapeutically effective concentration. If administered systemically, an amount between 0.01 and 100 mg per kg body weight per day, but preferably about 0.1 to 10 mg/kg, will effect a therapeutic result in most instances.

The retinoic acid like activity of these compounds was confirmed through the classic measure of retinoic acid activity involving the effects of retinoic acid on ornithine decarboxylase. The original work on the correlation between retinoic acid and decrease in cell proliferation was done by Verma & Boutwell, *Cancer Research*, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-O-tetradecanoylphorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in *Cancer Res.*: 1662-1670, 1975.

pounds of formula I when such synthesis is followed in fact and in spirit. The synthetic chemist will readily appreciate that the conditions set out here are specific embodiments which can be generalized to any and all of the compounds represented by formula I.

Compounds of formula I where X is —S— are prepared as per Reaction Scheme I.

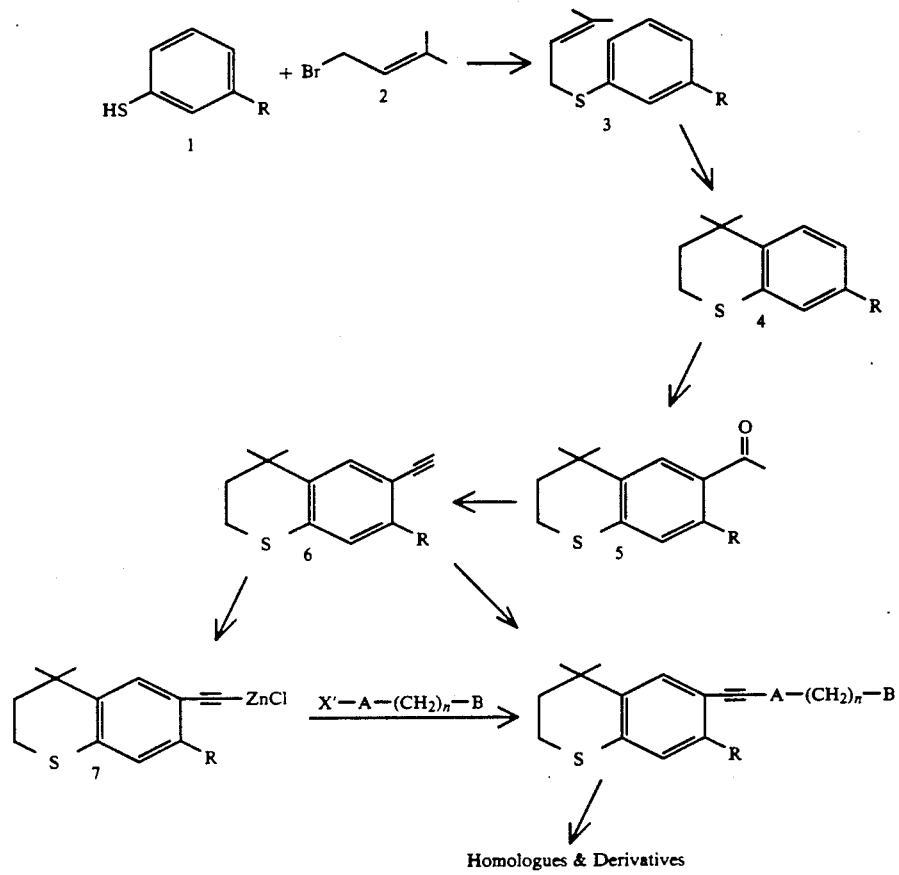

SPECIFIC EMBODIMENTS

The compounds of this invention can be made by a number of different synthetic chemical pathways. To illustrate this invention, there is here outlined a series of steps which have been proven to provide the com- Here, R is hydrogen or a lower alkyl group, A is defined above, n is 0-2 and B is H, or a protected acid, alcohol, aldehyde or ketone. X' is Cl, Br or I when n is 0 but preferably is Br or I when n is 1 or 2.

Alternatively, compounds of formula I where X is —S— are prepared as per Reaction Scheme II

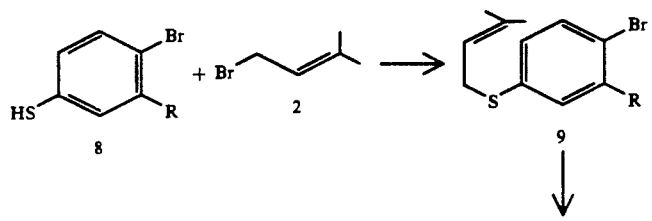

-continued

Reaction Scheme II

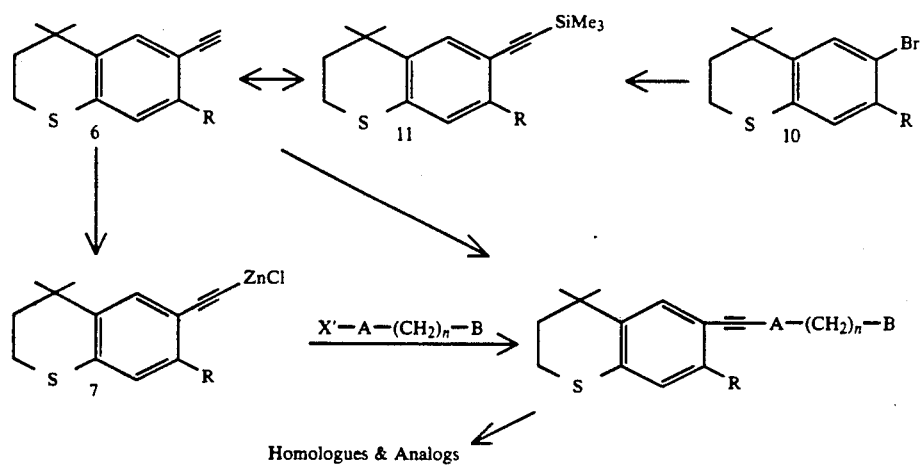

The definitions of R, n, A, B and X' are the same here as in Reaction Scheme I.

Compounds of formula I where X is oxygen are prepared as per Reaction Scheme III.

The definitions of R, n, A, B and X' are the same here as in Scheme I.

Compounds of formula I where X is N—R' where R' is hydrogen or alkyl are prepared as per Reaction Scheme IV.

Reaction Scheme III

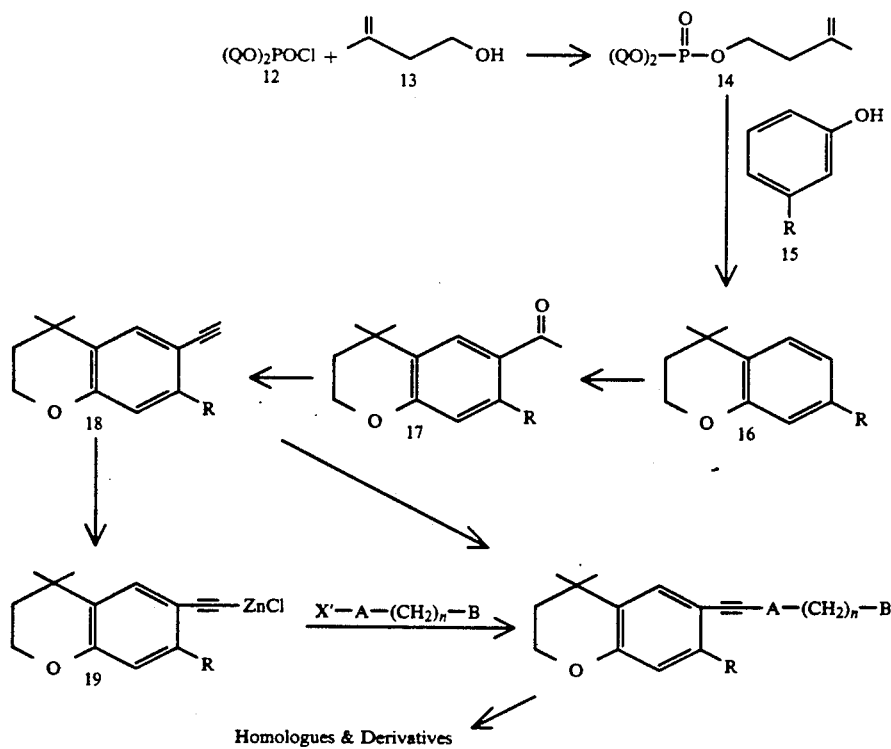

Reaction Scheme IV
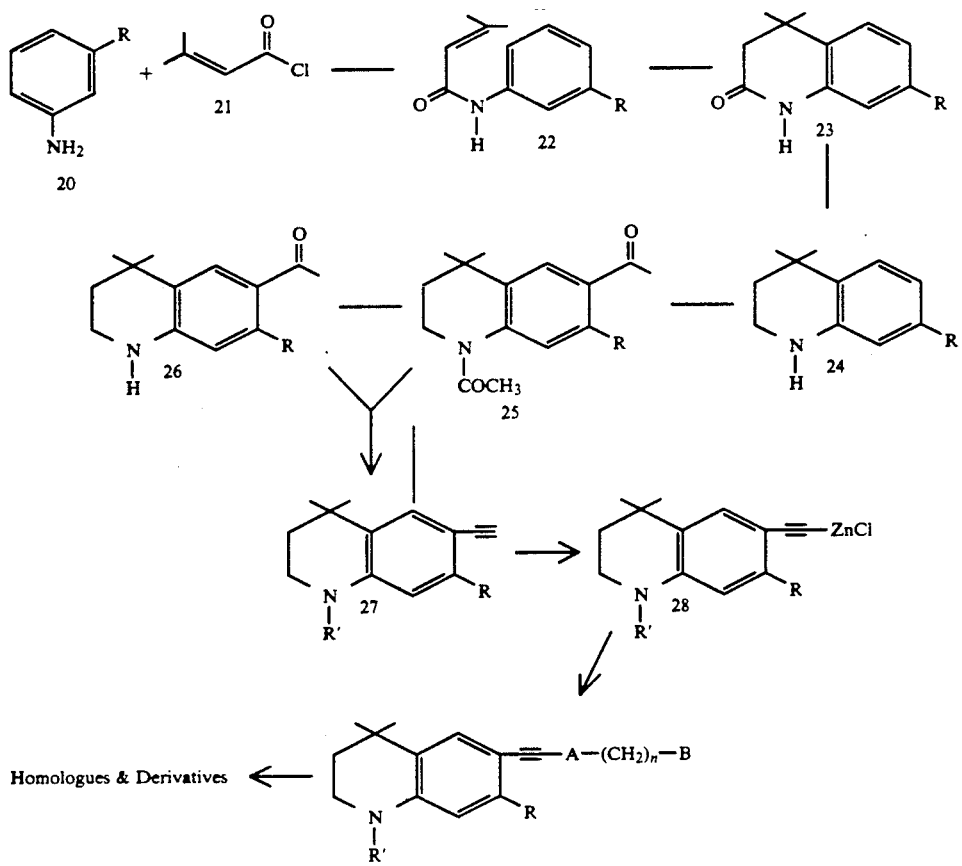
The definitions of R', n, A, B and X' are the same here as in Scheme I.
Alternatively, the sequence of steps outlined in Reaction Scheme V will serve to make such compounds where X is N—R' and R' is H or lower alkyl.
Reaction Scheme V
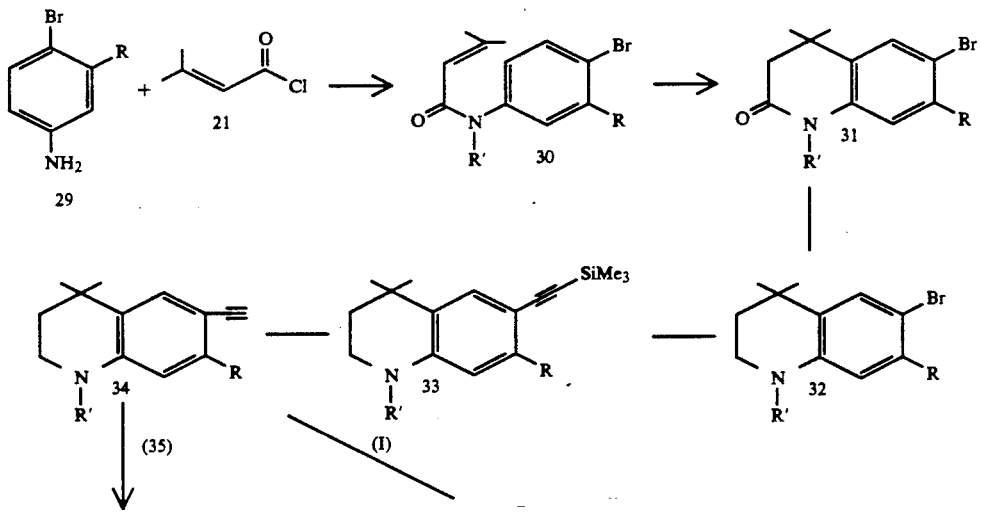

-continued
Reaction Scheme V

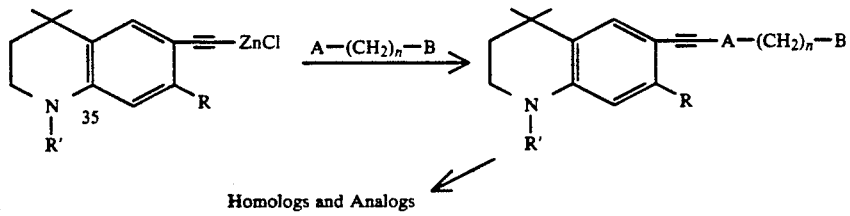

Homologs and Analogs

A general description for making each of the compounds recited in the foregoing Reaction Schemes follows.

In Reaction Scheme I, the following generalized reaction conditions are applicable. The thiophenol of formula 1 is first treated with approximately an equimolar amount of a strong base such as an alkali metal hydroxide, preferably sodium hydroxide, in acetone at reflux. Refluxing is carried out for between 1 and 4 hours, preferably 2.5 hours, after which the solution is treated with an equimolar amount of formula 2, 1-bromo-3-methyl-2-butene (Aldrich), dissolved in acetone. Refluxing is continued for about 2 days after which the solution is stirred for another 24 hours at about room temperature effecting formation of formula 3. It is isolated by conventional means.

Ring closure is effected by treating the sulfide (compound 3), whose formation is described above, with phosphorous pentoxide in the presence of phosphoric acid under an inert atmosphere to give the thiochroman of formula 4. The sulfide is first dissolved in an inert solvent such as benzene, toluene, or the like, and then treated with a small excess of phosphorous pentoxide along with concentrated phosphoric acid. The solution is heated at reflux with stirring under an inert gas such as argon or nitrogen for up to 24 hours. The product is then recovered and purified by conventional means.

The ketone of formula 5 is obtained by treating the thiochroman with acetyl chloride in the presence of aluminum chloride. A suspension of the aluminum chloride in a polar inert solvent is prepared under an inert atmosphere and at reduced temperature, i.e., $-10°$ to $10°$ C. The inert atmosphere may be argon or nitrogen, preferably argon. The reaction is conveniently carried out in a solvent such as methylene chloride. To the aluminum chloride suspension is added the thiochroman and acetyl chloride via a dropping funnel or similar device. About a 5% molar excess of acetyl chloride and 10% molar excess of aluminum chloride, relative to the thiochroman material, is used. The reaction is effected with agitation (stirring) over 0.5-4 hours at a temperature between $10°-50°$ C. Preferably the reaction is effected in about 2 hours at room temperature. Then the reaction is quenched with water and/or ice, the product extracted and further purified by distillation or some other appropriate means.

The acetylenic function of formula 6 is introduced by means of lithium diisopropylamide or a similar base at reduced temperature under an inert atmosphere. The reaction is carried out in an ether-type of solvent such as a dialkyl ether or a cyclic ether, for example, tetrahydrofuran, pyran or the like.

More specifically, lithium diisopropylamide is generated in situ by mixing diisopropylamine in a dry solvent such as tetrahydrofuran, which is then cooled, to between $-70°$ and $-50°$ C. under an inert atmosphere. An equimolar amount of an alkyllithium compound such as n-butyl lithium in an appropriate solvent is then added at the reduced temperature and mixed for an appropriate time to permit formation of lithium diisopropylamide (LDA). The ketone of formula 5 (at least a 10% molar excess) is dissolved in the reaction solvent, the solution cooled to that of the LDA mixture, and added to that solution. After brief mixing, the solution is then treated with a dialkyl chlorophosphate, preferably diethyl chlorophosphate in about a 20% molar excess. The reaction solution is then gradually brought to room temperature. This solution is then added to a second lithium diisopropylamide solution which is prepared in situ using dry solvent all under an inert atmosphere, preferably argon, at reduced temperature (e.g. $-78°$ C.). Thereafter, the reaction mixture is again warmed to room temperature where it is stirred for an extended period of time, preferably between 10 and 20 hours, most preferably about 15 hours. The solution is then acidified and the product recovered by conventional means.

Formula 7 compounds are prepared under conditions which exclude water and oxygen. A dry, ether-type solvent such as dialkyl ether or a cyclic ether such as a furan or pyran, particularly a tetrahydrofuran, may be used as the solvent. A solution of formula 6 is first prepared under an inert atmosphere such as argon or nitrogen, and then a strong base such as n-butyl lithium is added (in about a 10% molar excess). This reaction is begun at a reduced temperature of between $-10°$ and $+10°$ C., preferably about $0°$ C. The reaction mixture is stirred for a short period, between 30 minutes and 2 hours, and then treated with about a 10% molar excess of fused zinc chloride dissolved in the reaction solvent. This mixture is stirred for an additional 1-3 hours at about the starting temperature, then the temperature is increased to about ambient temperature for 10-40 minutes.

Where a protected heteroaromatic compound is needed to couple with formula 7 compounds, such may be prepared from their corresponding acids, alcohols, ketones or aldehydes. These starting materials, the protected acids, alcohols, aldehydes or ketones, are all available from chemical manufactures or can be prepared by published methods. Acids are esterified by refluxing the acid in a solution of the appropriate alcohol in the presence of thionyl chloride. Refluxing for 2-5 hours provides the desired ester. Alternatively, the acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p. 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of n before effecting a coupling reaction, where such compounds are not available from a commercial source, the heteroaromatics where B is —COOH are subjected to homologation by successive treatment under Arndt-Eistert conditions or other homologation procedures. These acids are then esterified by the general procedure outlined in the preceding paragraph. Alternatively, heteroaromatics where B is a different functional may also be homologated by appropriate procedures.

To effect the coupling of the thiochroman moiety with those of formula III, the halo-substituted heteroaromatic compound is dissolved in a dry reaction solvent. The heteromatic compound is used in an amount approximating the molar concentration of formula 7. This solution is introduced into a suspension of tetrakis-triphenylphosphine palladium (about a 5 to 10% molar amount relative to the reactants) in the reaction solvent at a temperature of between about $-10°$ and $+10°$ C. This mixture is stirred briefly, for about 15 minutes. To this just prepared mixture is then added the pre-prepared solution of formula 7, the addition being made at about room temperature. This solution is stirred for an extended period, between about 15 and 25 hours at room temperature. The reaction is then quenched with acid and the product separated and purified by conventional means to give the compounds of formula I.

An alternative means for making compounds where n is 1 or 2 is to subject the compounds of formula I where B is an acid or other function to homologation using the Arndt-Eistert method referred to above or other homologation procedures.

The acids and salts derived from formula I are readily obtainable from the corresponding esters. Basic saponification with an alkali metal base will provide the acid. For example, an ester of formula I may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about $-10°$ and $+10°$ C. The last mentioned solution is then stirred at the reduced temperature for 1-4 hours, preferably 2 hours. Solvent removal provides a residue which is taken up in an inert inorganic solvent such as benzene, cooled to about $0°$ C. and treated with concentrated ammonium hydroxide. The resulting mixture is stirred at a reduced temperature for 1-4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds where B is H are prepared from the corresponding halo-heterocyclic entity preferably where the halogen is I. This haloheterocyclic compound is reacted with the ethynyl entity or the ethynyl zinc chloride entity as represented in Reaction Scheme I and as illustrated in the Examples. Halo-substituted heterocyclic compounds where B is H are commercially available or can be prepared by methods in the literature.

Compounds where X is oxygen are prepared by the steps outlined in Reaction Scheme III. The phosphate of formula 14 is prepared from the corresponding diphenyl chlorophosphate and 3-methyl-3-butene-1-ol available from Aldrich or which may be prepared by means known in the art. It is preferred to prepare formula 14 by dissolving the alcohol of formula 13 in about a 10% excess of pyridine in a polar inert solvent under an inert atmosphere cooled to approximately $-10°$ to $10°$ C. This solution is then added drop-wise, under an inert atmosphere, to a solution of cooled diphenyl chlorophosphate in about an equal amount of the reaction solvent. About a 2-5% molar excess of diphenyl chlorophosphate relative to the alcohol is employed. The atmosphere may be argon, nitrogen, or another inert gas. The mixture is heated at reflux for between 1 and 5 hours, preferably about 3, to effect the reaction. The product is then recovered by conventional means.

The diphenyl phosphate ester from the preceding paragraph (formula 14) is then reacted with phenol or 3-alkylphenol to effect formation of compound 16. For example, phenol is added to a flask already containing stannic chloride under argon which has been cooled to between $-10°$ to $10°$ C. After thorough mixing of this combination for about 15 minutes to an hour at the reduced temperature, the phosphate is added at the reduced temperature. Both of these steps are carried out under an inert atmosphere such as argon or nitrogen. When the addition of the phosphate is completed, the mixture is stirred at about ambient temperature for up to 24 hours. Then the reaction is quenched with a dilute solution of aqueous alkali metal base or the like. The product is recovered by extraction and other conventional means.

Formula 16 is then acetylated, converted to the acetylene and either the acetylene or the corresponding alkynyl zinc chloride salt coupled with the appropriate heterocycle by the steps outlined in Reaction Scheme I.

The tetrahydroquinoline moiety, that is where X is nitrogen, can be made by the steps outlined in Reaction Scheme IV in part by the method described in European Patent Application 0130795 published Sept. 1, 1985. First, 3-methylcrotonoyl chloride is reacted with aniline to obtain the amide. This amide is then cyclized using aluminum chloride in the absence of solvent. Lithium aluminum hydride or another acceptable reducing agent of similar type is then used to reduce the 2-oxo-1,2,3,4-tetrahydroquinoline, preferably in an inert solvent such as diethyl ether. This amine is then acetylated using acetyl chloride in a polar solvent such as pyridine. This protected amine is then acetylated in the presence of aluminum chloride. The acetyl function on the nitrogen may then be removed by base hydrolysis. Then the acetylated compound is converted to the acetylene and ZnCl salt as outlined in Reaction Scheme I. The acetylene or the salt is then coupled with an appropriate compound of formula III as described before to give compounds of formula I.

Reaction Scheme V sets out an alternative method for making the tetrahydroquinoline compounds illustrated in Reaction Scheme IV.

The following Examples are set out to illustrate the invention, not to limit its scope.

EXAMPLE 1

Phenyl-3-methylbut-2-enylsulfide

A mixture of 14.91 g (135.324 mmol) of thiophenol and 5.5 g (137.5 mmol) of NaOH in 100 ml acetone was heated at reflux for 2.5 hours and then treated dropwise with a solution of 20 g (134.19 mmol) of 1-bromo-3-methyl-2-butene in 20 ml acetone. This solution was refluxed for 40 hours and then stirred at room temperature for 24 hours. Solvent was then removed in vacuo, the residue taken up in water, and extracted with 3×50 ml ether. Ether extracts were combined and washed with 3×30 ml of 5% NaOH solution, then water, saturated NaCl solution and dried (MgSO$_4$). Solvent was then removed in vacuo and the residue further purified by kugelrohr distillation (80° C., 0.75 mm) to give the title compound as a pale yellow oil.

PMR (CDCl$_3$): δ1.57 (3H, s), 1.69 (3H, s), 3.52 (2H, d, J~7.7 Hz), 5.29 (1H, t, J~7.7 Hz), 7.14 (1H, t, J~7.0 Hz), 7.24 (2H, t, J~7.0 Hz), 7.32 (2H, d, J~7.0 Hz).

EXAMPLE 2

4,4-Dimethylthiochroman

To a solution of 15.48 g (86.824 mmol) of phenyl-3-methylbut-2-enylsulfide (from Example 1) in 160 ml benzene were added successively 12.6 g (88.767 mmol) of phosphorus pentoxide and 11 ml of 85% phosphoric acid. This solution was refluxed with vigorous stirring under argon for 20 hours, then cooled to room temperature. The supernatant organic layer was decanted and the syrupy residue extracted with 3×50 ml ether. Organic fractions were combined and washed with water, saturated NaHCO$_3$ and saturated NaCl solution and then dried (MgSO$_4$). Solvent was removed in vacuo and the residue purified by kugelrohr distillation (80° C., 0.5 mm) to give the title compound as a pale yellow oil.

PMR (CDCl$_3$): δ1.30 (6H, s), 1.90-1.95 (2H, m), 2.95-3.00 (2H, m), 6.96-7.00 (2H, m), 7.04-7.07 (1H, m), 7.30-7.33 (1H, m).

This method can be used to make 7-position alkyl analogues as exemplified by the following compounds: 4,4,7-trimethylthiochroman; 4,4-dimethyl-7-ethylthiochroman; 4,4-dimethyl-7-propylthiochroman; 4,4-dimethyl-7-butylthiochroman; and 4,4-dimethyl-7-hexylthiochroman.

EXAMPLE 3

4,4Dimethyl-6-acetylthiochroman

A solution of 14.3 g (80.21 mmol) of 4,4-dimethyl thiochroman (from Example 2) and 6.76 g (86.12 mmol) of acetyl chloride in 65 ml benzene was cooled in an ice bath and treated dropwise with 26.712 g (102.54 mmol) of stannic chloride. The mixture was stirred at room temperature for 12 hours, then treated with 65 ml water and 33 ml conc. hydrogen chloride and heated at reflux for 0.5 hours. After being cooled to room temperature, the organic layer was separated and the aqueous layer extracted with 5×50 ml benzene. The recovered organic fractions were combined and washed with 5% sodium carbonate solution, water, saturated NaCl solution and then dried (MgSO$_4$). The solvent was removed in vacuo and the residue purified by flash chromatography (silica; 5% ethyl acetate in hexanes) followed by kugelrohr distillation (150° C., 0.7 mm) to give the title compound as a pale yellow oil.

PMR (CDCl$_3$): δ1.35 (6H, s), 1.92-1.98 (2H, m) 2.54 (3H, s), 3.02-3.08 (2H, m), 7.13 (1H, d, J~8.6 Hz), 7.58 (1H, dd, J~8.6 Hz, 2 Hz), 7.99 (1H, d, J~2 Hz).

This same method may be used to acetylate all compounds made as per Example 2.

EXAMPLE 4

4,4-Dimethyl-6-ethynylthiochroman

To a solution of 1.441 g (14.2405 mmol) of diisopropylamine in 30 ml dry tetrahydrofuran under argon at −78° C. was added dropwise 9 ml of 1.6M (14.4 mmol) n-butyllithium in hexane. After stirring this solution at −78° C. for 1 hour, it was treated dropwise with a solution of 2.95 g (13.389 mmol) of 4,4-dimethyl-6-acetylthiochroman in 5 ml of dry tetrahydrofuran. After another hour of stirring at −78° C., the solution was treated with 2.507 g (14.53 mmol) of diethyl chlorophosphate and brought to room temperature, where it was stirred for 3.75 hours. This solution was then transferred using a double ended needle to a solution of lithium diisopropylamide (prepared as above using 2.882 g (28.481 mmol) of diisopropylamine and 18 ml of 1.6M (28.8 mmol) n-butyllithium in hexane) in 60 ml dry tetrahydrofuran at −78° C. The cooling bath was removed and the solution stirred at room temperature for 15 hours, then quenched with water and acidified to pH 1 with 3N hydrogen chloride. The mixture was stirred at room temperature for 12 hours, then treated with 65 ml water and 33 ml conc. hydrogen chloride and heated at reflux for 0.5 hours. After being cooled to room temperature, the organic layer was separated and the aqueous layer extracted with 5×50 ml benzene. The recovered organic fractions were combined and washed with 5% sodium carbonate solution, water, saturated NaCl solution and then dried (MgSO$_4$). The solvent was removed in vacuo and the residue purified by flash chromatography (silica; 5% ethyl acetate in hexanes)

followed by kugelrohr distillation (150° C., 0.7 mm) to give the captioned compound as a pale yellow oil.

PMR (CDCl$_3$): δ1.35 (6H, s), 1.92–1.98 (2H, m) 2.54 (3H, s), 3.02–3.08 (2H, m), 7.13 (1H, d, J~8.6 Hz), 7.58 (1H, dd, J~8.6 Hz, 2 Hz), 7.99 (1H, d, J~2 Hz).

In the same manner, all acetyl-containing compounds prepared under Example 3 may be converted to their corresponding ethynyl analogues.

EXAMPLE 5

Ethyl 6-chloronicotinate

A mixture of 15.75 g (0.1 mol) 6-chloronicotinic acid, 6.9 g (0.15 mol) ethanol, 22.7 g (0.11 mol) dicyclohexylcarbodiimide and 3.7 g dimethylaminopyridine in 200 ml methylene chloride was heated at reflux for 2 hours. The mixture was allowed to cool, solvent removed in vacuo and residue subjected to flash chromatography to give the title compound as a low-melting white solid.

PMR (CDCl$_3$): δ1.44 (3H, t, J~6.2 Hz) 4.44 (2H, q, J~4.4 Hz), 7.44 (1H, d, J~8.1 Hz), 8.27 (1H, dd, J~8.1 Hz, 3 Hz), 9.02 (1H, d, J~3 Hz).

This procedure may be used to esterify any of the other halo-substituted acids employed in the making of these compounds such as
ethyl 2-(2-chloropyrid-5-yl)acetate;
ethyl 5-(2-chloropyrid-5-yl)pentanoate;
ethyl 2-(2-iodofur-5-yl)acetate;
ethyl 5-(2-iodofur-5-yl)pentanoate;
ethyl 2-(2-iodothien-5-yl)acetate;
ethyl 5-(2-iodothien-5-yl)pentanoate;
ethyl 2-(3-chloropyridazin-6-yl)acetate;
ethyl 5-(3-chloropyridazin-6-yl)pentanoate; and the corresponding chloro, or other halo, substituted pyrimidinyl or pyrazinyl analogues of such esters.

EXAMPLE 6

Ethyl 6-[2-(4,4-dimethylthiochroman-6-yl)ethynyl]nicotinate

Reaction vessels used in this procedure were flame dried under vacuum and all operations carried out in an oxygen-free, argon or nitrogen atmosphere. To a solution of 465.7 mg (2.3019 mmol) of 4,4-dimethyl-6-ethynyl-thiochroman in 4 ml of dry tetrahydrofuran at 0° C. was added dropwise 1.5 ml of 1.6M (2.4 mmol) n-butyl-lithium in hexane. This was stirred at 0° C. for 10 minutes and at room temperature for 10 minutes, cooled again to 0° C. and then treated with a solution of 330 mg (2.4215 mmol) of fused ZnCl$_2$ in 4 ml dry tetrahydrofuran using a double ended needle. Thereafter the solution was stirred at 0° C. for 30 minutes, then at room temperature for 10 minutes. A solution of 426.3 mg (2.2967 mmol) of ethyl 6-chloronicotinoate (from Example 5) in 4 ml dry tetrahydrofuran was transferred by double ended needle into a suspension of 430 mg (0.37 mmol) of tetrakistriphenylphosphine palladium in 4 ml dry tetrahydrofuran and stirred at room temperature for 10 minutes, then treated by double ended needle with the solution of the alkynylzinc prepared above. This mixture was stirred at room temperature for 18 hours, then quenched with 100 ml water. Product was recovered by extraction with 3×75 ml ether. Ether fractions were combined and washed with saturated NaCl solutions and dried (mgSO$_4$). Solvent was removed in vacuo and the residue purified by flash chromatography (silica; 5% ethyl acetate in hexane) followed by HPLC (Whatman Partisil M-9 10/50; 4% ethyl acetate in hexane) to give the title compound as a white solid.

PMR (CDCl$_3$): δ1.36 (6H, s), 1.45 (3H, t, J~7 Hz), 1.96–2.00 (2H, m), 3.05–3.09 (2H, m), 4.45 (2H, q, J~7 Hz), 7.11 (1H, d, J~8.4 Hz), 7.29 (1H, dd, J~8.4 Hz, 2.2 Hz), 7.59 (1H, d, J~7.8 Hz), 7.66 (1H, d, J~2.2 Hz), 8.30 (1H, dd, J~7.8 Hz, 2.3 Hz), 9.22 (1H, d, J~2.3 Hz).

Using this method, but substituting the appropriate ethynylthiochroman from Example 4 and the appropriate halo-substituted heteroaromatic ester from Example 5, the following compounds may be prepared:
ethyl 6-(2(4,4,7-trimethylthiochroman-6-yl)-ethynyl)-nicotinate;
ethyl 6-(2-4,4-dimethyl-7-ethylthiochroman-6-yl)-ethynyl)nicotinate;
ethyl 6-(2-(4,4-dimethyl-7-propylthiochroman-6-yl)-ethynyl)nicotinate;
ethyl 6-(2-(4,4-dimethyl-7-hexylthiochroman-6-yl)-ethynyl)nicotinate;
ethyl (2-((4,4-dimethylthiochroman-6-yl)ethynyl)pyrid-5-yl)acetate;
ethyl (2-((4,4,7-trimethylthiochroman-6-yl)ethynyl)pyrid-5-yl)acetate;
ethyl (2-((4,4-dimethyl-7-ethylthiochroman-6-yl)-ethynyl)pyrid-5-yl)acetate;
ethyl (2-((4,4-dimethyl-7-hexylthiochroman-6-yl)-ethynyl)pyrid-5-yl)acetate;
ethyl 3-(2-((4,4-dimethylthiochroman-2-yl)-ethynyl)pyrid-5-yl)propionate;
ethyl 3-(2-((4,4,7-trimethylthiochroman-6-yl)-ethynyl)-pyrid-5-yl)propionate;
ethyl 3-(2((4,4-dimethyl-7-ethylthiochroman-6-yl)-ethynyl)pyrid-5-yl)propionate;
ethyl 3-(2((4,4-dimethyl-7-hexylthiochroman-6-yl)-ethynyl)pyrid-5-yl)propionate;
ethyl 5-(2-((4,4-dimethylthiochroman-6-yl)ethynyl)pyrid-5-yl)pentanoate;
ethyl 5-(2-((4,4,7-trimethylthiochroman-6-yl)ethynyl)-pyrid-5-yl)pentanoate;
ethyl 5-(2-((4,4-dimethyl-7-ethylthiochroman-6-yl)ethynyl)pyrid-5-yl)pentanoate;
ethyl (5-((4,4-dimethylthiochroman-6-yl)ethynyl)fur-2-yl)acetate;
ethyl (5-((4,4,7-trimethylthiochroman-6-yl)ethynyl)fur-2-yl)acetate;
ethyl (5-((4,4-dimethyl-7-ethylthiochroman-6-yl)ethynyl)fur-2-yl)acetate;
ethyl (5-((4,4-dimethyl-7-hexylthiochroman-6-yl)ethynyl)fur-2-yl)acetate;
ethyl 5-(5-((4,4-dimethylthiochroman-6-yl)ethynyl)fur-2-yl)pentanoate;
ethyl 5-(5-((4,4,7-trimethylthiochroman-6-yl)ethynyl)-fur-2-yl)pentanoate;
ethyl 5-(5-((4,4-dimethyl-7-ethylthiochroman-6-yl)ethynyl)fur-2-yl)pentanoate;
ethyl 5-(5-((4,4-dimethyl-7-hexylthiochroman-6-yl)ethynyl)fur-2-yl)pentanoate;
ethyl (5-((4,4-dimethylthiochroman-6-yl)ethynyl)thien-2-yl)acetate;
ethyl (5-((4,4,7-trimethylthiochroman-6-yl)ethynyl)thien-2-yl)acetate;
ethyl (5-((4,4-dimethyl-7-ethylthiochroman-6-yl)ethynyl)thien-2-yl)acetate;
ethyl (5-((4,4-dimethyl-7-hexylthiochroman-6-yl)ethynyl)thien-2-yl)acetate;
ethyl 5-(5-((4,4-dimethylthiochroman-6-yl)ethynyl)thien-2-yl)pentanoate;
ethyl 5-(5-((4,4,7-trimethylthiochroman-6-yl)ethynyl)-thien-2-yl)pentanoate;

ethyl 5-(5-((4,4-dimethyl-7-ethylthiochroman-6-yl)ethynyl)thien-2-yl)pentanoate;
ethyl 5-(5-((4,4-dimethyl-7-hexylthiochroman-6-yl)ethynyl)thien-2-yl)pentanoate;
ethyl (6-((4,4-dimethylthiochroman-6-yl)ethynyl)pyridazin-3-yl)acetate;
ethyl (6-((4,4,7-trimethylthiochroman-6-yl)ethynyl)pyridazin-3-yl)acetate;
ethyl (6-((4,4-dimethyl-7-ethylthiochroman-6-yl)ethynyl)pyridazin-3-yl)acetate;
ethyl (6-((4,4-dimethyl-7-hexylthiochroman-6-yl)ethynyl)pyridazin-3-yl)acetate;
ethyl 5-(6-((4,4-dimethylthiochroman-6-yl)ethynyl)pyridazin-3-yl)pentanoate;
ethyl 5-(6-((4,4,7-trimethylthiochroman-6-yl)ethynyl)pyridazin-3-yl)pentanoate;
ethyl 5-(6-((4,4-dimethyl-7-ethylthiochroman-6-yl)ethynyl)pyridazin-3-yl)pentanoate;
ethyl 5-(6-((4,4-dimethyl-7-hexylthiochroman-6-yl)ethynyl)pyridazin-3-yl)pentanoate;
ethyl (5-((4,4-dimethylthiochroman-6-yl)ethynyl)pyrimidin-2-yl)acetate;
ethyl (5-((4,4,7-trimethylthiochroman-6-yl)ethynyl)pyrimidin-2-yl)acetate;
ethyl (5-((4,4-dimethyl-7-ethylthiochroman-6-yl)thynyl)pyrimidin-2-yl)acetate;
ethyl (5-((4,4-dimethyl-7-hexylthiochroman-6-yl)ethynyl)pyrimidin-2-yl)acetate;
ethyl 5-(5-((4,4-dimethylthiochroman-6-yl)ethynyl)pyrimidin-2-yl)pentanoate;
ethyl 5-(5-((4,4,7-trimethylthiochroman-6-yl)ethynyl)pyrimidin-2-yl)pentanoate;
ethyl 5-(5-((4,4-dimethyl-7-ethylthiochroman-6-yl)ethynyl)pyrimidin-2-yl)pentanoate;
ethyl 5-(5-((4,4-dimethyl-7-hexylthiochroman-6-yl)ethynyl)pyrimidin-2-yl)pentanoate;
ethyl (5-((4,4-dimethylthiochroman-6-yl)ethynyl)pyrazin-2-yl)acetate;
ethyl (5-((4,4,7-trimethylthiochroman-6-yl)ethynyl)pyrazin-2-yl)acetate;
ethyl (5-((4,4-dimethyl-7-ethylthiochroman-6-yl)ethynyl)pyrazin-2-yl)acetate;
ethyl (5-((4,4-dimethyl-7-hexylthiochroman-6-yl)ethynyl)pyrazin-2-yl)acetate;
ethyl 5)5-((4,4-dimethylthiochroman-6-yl)ethynyl)pyrazin-2-yl)pentanoate;
ethyl 5-(5-((4,4,7-trimethylthiochroman-6-yl)ethynyl)prazin-2-yl)pentanoate;
ethyl 5-(5-((4,4-dimethyl-7-ethylthiochroman-6-yl)ethynyl)pyrazin-2-yl)pentanoate; and
ethyl 5-(5-((4,4-dimethyl-7-hexylthiochroman-6-yl)ethynyl)pyrazin-2-yl)pentanoate.

Alternative synthesis: The title compound of Example 6, ethyl 6-[2-(4,4-dimethylthiochroman-6-yl)ethynyl]nicotinate, was also prepared as follows.

A solution of 15.4 g (76.2 mmol) of 4,4-dimethyl-6-ethynylthiochroman and 14.0 g (75.5 mmol) of ethyl-6-chloronicotinate in 35 ml of freshly distilled triethylamine was degassed and then treated under nitrogen with a finely powdered mixture of 1 g (5.25 mmol) of high purity cuprous iodide and 2 g (2.85 mmol) of bis(triphenylphosphine) palladium (II) chloride. The mixture was heated under nitrogen at 55° C. for 20 hours and then cooled to room temperature. The triethylamine was then removed under vacuum and the residue was diluted with 200 ml of a 1:4 mixture of ethyl acetate and hexanes. This mixture was filtered through silica and the filtrate concentrated in vacuo. The resultant residue was purified by flash chromatography (silica gel; 15% ethyl acetate in hexanes) and recrystallized from a mixture of ethyl acetate and hexanes to give the title compound as a pale yellow solid.

EXAMPLE 7

(3-Methyl-4-bromo-phenyl)-3-methylbut-2-enylsulfide

To a stirred solution of 9.52 g (68 mmol) of 3-methyl-4-bromothiophenol in 80 ml of acetone was added 2.86 g (68 mmol) of powdered sodium hydroxide. This mixture was stirred until the components were dissolved. The reaction mixture was then heated to reflux, and then treated with a solution of 11.26 g (68 mmol) of 4-bromo-2-methyl-2-butene in 20 ml of acetone. The mixture was heated at reflux for a further 0.5 hour, cooled to room temperature and the solvent removed in vacuo. The residue was taken up in 35 ml of water and extracted with ether. The ether extracts were combined and washed successively with water and saturated NaCl solution and then dried (MgSO$_4$). The solvent was removed in vacuo and the residue kugelrohr distilled (140°-145° C., 0.2 mm) to give the title compound as a colorless oil.

PMR (CDCl$_3$): δ1.58 (3H, s), 1.70 (3H, s), 2.33 (3H, s), 3.49 (2H, d, J~7.8 Hz), 5.26 (1H, t, J~7.8 Hz), 6.98 (1H, dd, J~8.3 Hz, 2.3 Hz), 7.17 (1H, d J~2.3 Hz), 7.38 (1H, d, J~8.3 Hz).

EXAMPLE 8

4,4,7-Trimethyl-6-bromothiochroman

To 40 g of a vigorously stirred mixture of 10% phosphorous pentoxide in methanesulfonic acid was added slowly 6.0 g (28.8 mmol) of (3-methyl-4-bromophenyl)-3-methylbut-2-enylsulfide. The mixture was stirred at room temperature for a further 2 hours and was then poured onto ice. The mixture was extracted with 2×40 ml of ether and the combined ether extracts were washed successively with water and saturated NaCl solution and then dried. The solvent was removed in vacuo and the residue distilled using a kugelrohr apparatus (130° C.; 0.07 mm) to give the title compound as a viscous oil.

PMR (CDCl$_3$): δ1.28 (6H, s) 1.84-1.93 (2H, m), 2.26 (3H, s), 2.95-3.03 (2H, m), 6.94 (1H, s), 7.46 (1H, s).

EXAMPLE 9

4,4,7-Trimethyl-6-trimethylsilylethynylthiochroman

A mixture of 624 mg (3.0 mmol) of 4,4,7-trimethyl-6-bromothiochroman, 314 mg (3.2 mmol) of trimethylsilylacetylene, 40 mg (0.21 mmol) of cuprous iodide, 80 mg (0.11 mmol) of bis-(triphenylphosphine) palladium (II) chloride and 1 ml of triethylamine was degassed under nitrogen and heated in a sealed tube at 85° C. for 15 hours. The mixture was then treated with a further 20 mg (0.11 mmol) of cuprous iodide and 40 mg (0.06 mmol) of the palladium (II) catalyst. The mixture was then heated under a nitrogen atmosphere in the sealed tube at 100° C. for a further 64 hours. The triethylamine was then removed under vacuum and the residue purified by flash chromatography (silica; hexanes) to give the title compound as a yellow oil.

PMR (CDCl$_3$): δ0.28 (9H, s), 1.30 (6H, s), 1.88-1.97 (2H, m), 2.33 (3H, s), 2.97-3.05 (2H, m), 6.92 (1H, s), 7.43 (1H, s).

EXAMPLE 10

4,4,7-Trimethyl-6-ethynylthiochroman

A mixture of 380 mg (1.69 mmol) of 4.4.7-trimethy-6-trimethylsilylethynylthiochroman, 4 ml of isopropanol and 2.5 ml of aqueous 1N potassium hydroxide was degassed under nitrogen and stirred at room temperature for 16 hours. The mixture was concentrated under vacuum and extracted with 2×10 ml of ether. The ether extracts were combined and washed successively with water and saturated NaCl solution and then dried (MgSO$_4$). The solvent was removed in vacuo to give the title compound as a yellow oil.

PMR (CDCl$_3$): δ1.31 (6H, s), 1.88-1.96 (2H, m), 2.35 (3H, s), 3.00-3.08 (2H, m), 3.25 (1H, s), 6.94 (1H, s), 7.47 (1H, s).

EXAMPLE 11

Ethyl 6-[2-(4,4,7-trimethylthiochroman-6-yl)ethynyl]nicotinate

A mixture of 86 mg (0.4 mmol) of 4,4,7-trimethyl-6-ethynylthiochroman, 85 mg (0.46 mmol) of ethyl 6-chloronicotinate and 0.8 ml of triethylamine was degassed under nitrogen and then treated with a mixture of 10 mg (0.05 mmol) of cuprous iodide and 20 mg (0.03 mmol) of bis(triphenylphosphine) palladium (II) chloride. The reaction mixture was heated at 55° C. under a nitrogen atmosphere for 18 hours. The mixture was then extracted with 1.5 ml of 40% ethyl acetate in hexanes and purified by flash chromatography (silica; 10% ethyl acetate in hexanes) to give the title compound as a yellow solid.

PMR (CDCl$_3$): δ1.32 (6H, s), 1.43 (3H, t, J~7.2 Hz), 2.44 (3H, s), 3.01-3.05 (2H, m), 4.42 (2H, q, J~7.2 Hz), 6.98 (1H, s), 7.54-7.63 (2H, m), 8.27 (1H, dd, J~8.3 Hz, 2.3 Hz), 9.21 (1H, d, J~2.3 Hz).

EXAMPLE 12

Ethyl 5-(2-(4,4-dimethyl-thiochroman-6-yl)ethynyl)thiophene-2-carboxylate

Using the same general procedure described in the preceeding Example 11, but using instead 4,4-dimethyl-6-ethynylthiochroman and ethyl 5-bromothiophene-2-carboxylate, the title compound was synthesized.

PMR (CDCl$_3$): δ1.31 (6H, s), 1.36 (3H, t, J~7.5 Hz), 1.90-1.94 (2H, m), 2.99-3.03 (2H, m), 4.33 (2H, q, J~7.5 Hz), 7.04 (1H, d, J~8.1 Hz), 7.13-7.18 (2H, m), 7.50 (1H, s), 7.65 (1H, d, J~3.9 Hz).

EXAMPLE 13

Ethyl-5-(2-(4,4-dimethylthiochroman-6-yl)ethynyl)-2-furoate

Again using the general procedure of Example 11, but using instead 4,4-dimethyl-6-ethynylthiochroman and ethyl 5-bromo-2-furate, the title compound was synthesized.

PMR (CDCl$_3$): δ1.24 (6H, s), 1.31 (3H, t, J~7.0 Hz), 1.83-1.87 (2H, m), 2.93-2.97 (2H, m), 4.30 (2H, q, J~7.0 Hz), 6.60 (1H, d, J~3.4 Hz), 6.98 (1H, d, J~8.1 Hz), 7.09-7.11 (2H, m), 7.46 (1H, d, J~1.7 Hz).

EXAMPLE 14

Diphenyl-3-methyl-3-buten-1-yl phosphate

To an ice-cooled solution of 12.2 g (141.65 mmol) of 3-methyl-3-buten-1-ol (Aldrich) and 11.9 g (150.44 mmol) of pyridine in 100 ml of tetrahydrofuran was added dropwise under argon a solution of 38.5 g (143.21 mmol) of diphenyl chlorophosphate 93 in 100 ml of tetrahydrofuran. The mixture was heated at reflux for 3 hours and then cooled and filtered. The filtrate was concentrated in vacuo and the residue dissolved in 400 ml of 1:1 ether and hexane and then washed with 2×200 ml water, 75 ml saturated NaCl solution and dried (MgSO$_4$). The solvent was removed in vacuo to give the captioned compound as a pale yellow oil.

PMR (CDCl$_3$): δ1.69 (3H, M), 2.37 (2H, t, J N7 Hz), 4.32 (2H, q, J~7 Hz), 4.72 (1H, M), 7.10-7.35 (10H, m).

EXAMPLE 15

4,4-Dimethylchroman

To a dry, ice-cooled flask containing 34.95 g (0.134 mol) of stannic chloride was added quickly under argon 63.0 g (0.669 mol) of phenol. The mixture was stirred at 0° C. for 0.5 hour and then treated with 43.0 g (0.135 mol) of diphenyl-3-methyl-3-buten-1-yl phosphate, followed by a 5 ml carbon disulfide rinse. The mixture was stirred at room temperature for 21 hours and then quenched by pouring onto 700 g ice and 1 liter of 1.5N NaOH. The mixture was extracted with 1×600 ml and 2×300 ml ether. The combined ether fractions were washed with 2N NaOH, saturated NaCl and dried (MgSO$_4$). Solvent was removed in vacuo and the residue purified by flash chromatography (silica; 2% ether in hexane) to give the title compound as a colorless oil.

PMR (CDCl$_3$): δ1.34 (6H, M), 1.80-1.85 (2H, m), 4.15-4.20 (2H, m), 6.80 (1H, dd, J~8.1 Hz, 1.5 Hz), 6.87 (1H, td, J~8.1 Hz, 1.5 Hz), 7.07 (1H, td, J~8.1 Hz, 1.5 Hz), 7.26 (1H, dd, J~8.1 Hz, 1.5 Hz).

This method also serves to prepare the corresponding 7-alkylchroman compounds, starting with the appropriate 3-alkylphenol, for example:
4,4,7-trimethylchroman;
4,4-dimethyl-7-ethylchroman;
4,4-dimethyl-7-propylchroman;
4,4-dimethyl-7-butylchroman;
4,4-dimethyl-7-pentylchroman; and
4,4-dimethyl-7-hexylchroman.

EXAMPLE 16

4,4-Dimethyl-6-acetylchroman

To a stirred solution of 7.94 g (48.9425 mmol) of 4,4-dimethylchroman in 70 ml of nitromethane was added under argon 4.0 g (50.96 mmol) of acetyl chloride followed by 6.8 g (51 mmol) of aluminum chloride. This was stirred at room temperature for 5.5 hours and then cooled in an ice bath and treated slowly with 70 ml 6N hydrogen chloride. The resultant mixture was stirred at room temperature for 10 minutes, then treated with 100 ml ether and the organic layer separated. The organic layer was washed with water, saturated NaHCO$_3$ and saturated NaCl solutions and dried (MgSO$_4$). Solvent was removed in vacuo and the residue purified by flash chromatography (silica; 10% ethyl acetate in hexanes). This was followed by kugelrohr distillation (95°-100° C.; 0.15 mm) to give the title compound as a colorless oil.

PMR (CDCl$_3$): δ1.40 (6H, M), 1.95-2.00 (2H, m), 2.58 (3H, M), 4.25-4.30 (2H, m), 6.83 (1H, d, J~8.0 Hz), 7.62 (1H, dd, J~8.0 Hz, 1.5 Hz), 8.00 (1H, d, J~1.5 Hz).

Following the same procedure and using the compounds of Example 15, the following compounds can be prepared:
4,4-dimethyl-6-acetyl-7-methylchroman;
4,4-dimethyl-6-acetyl-7-ethylchroman;
4,4-dimethyl-6-acetyl-7-propylchroman;
4,4-dimethyl-6-acetyl-7-butylchroman;
4,4-dimethyl-6-acetyl-7-pentylchroman; and
4,4-dimethyl-6-acetyl-7-hexylchroman.

EXAMPLE 17

4,4-Dimethyl-6-ethynylchroman

To a solution of 2.47 g (24.41 mmol) of diisopropylamine in 40 ml dry tetrahydrofuran under argon at −78° C. was added dropwise 15.2 ml of 1.6M (24.32 mmol) n-butyl lithium in hexane. Mixture was stirred at −78° C. for 1 hour and then treated dropwise with a solution of 4.98 g (24.38 mmol) of 4,4-dimethyl-6-acetylchroman in 4 ml of dry tetrahydrofuran. After stirring at −78° C. for 1 hour, the solution was treated with 4.2 g (24.36 mmol) of diethyl chlorophosphate. The cooling bath was then removed and mixture stirred at room temperature for 2.75 hours. This solution was then transferred using a double ended needle to a solution of lithium diisopropyl amide (prepared as per Example 4) using 4.95 g (48.92 mmol) of diisopropylamine and 30.5 ml of 1.6M (48.8 mmol) n-butyl lithium in hexane in 80 ml dry tetrahydrofuran at −78° C. The cooling bath was removed and mixture stirred at room temperature for 18 hours and then quenched with 50 ml water and 25 ml of 3N hydrogen chloride. The mixture was extracted with 2×100 ml and 3×50 ml of pentane and the combined organic fractions washed with 3N hydrogen chloride, water, saturated NaHCO$_3$ and saturated NaCl solution and then dried (MgSO$_4$). Solvent was then removed in vacuo and the residue purified by flash chromatography (silica; 10% ethyl acetate in hexane) followed by kugelrohr distillation (70° C.; 0.35 mm) to give the title compound as a colorless crystalline solid.

PMR (CDCl$_3$): δ1.33 (6H, s), 1.81-1.86 (2H, m), 3.00 (1H, s), 4.19-4.24 (2H, m), 6.75 (1H, d, J~8.5 Hz), 7.22 (1H, dd, J~8.5 Hz, 2.3 Hz), 7.44 (1H, d, J~2.3 Hz).

This procedure serves to convert all acetyl-containing compounds prepared as per Example 16 to their corresponding ethynyl-containing compounds.

EXAMPLE 18

Ethyl 6-[2-(4,4-dimethylchroman-6-yl)ethynyl]nicotinate

Reaction vessels used in this procedure were flame dried under vacuum and all operations were carried out in an oxygen-free, argon or nitrogen atmosphere. To a solution of 509.4 mg (2.74 mmol) of 4,4-dimethyl-6-ethynylchroman in 4 ml of dry tetrahydrofuran at 0° C. was added dropwise 1.72 ml of 1.6M (2.75 mmol) of n-butyl lithium in hexane. Stirring was commenced at 0° C. for 30 minutes and at room temperature for 15 minutes, after which the solution was cooled again to 0° C. and then treated with a solution of 380 mg (2.79 mmol) of fused zinc chloride in 5 ml of dry tetrahydrofuran using a double ended needle. The resulting solution was stirred at 0° C. for 1 hour and then at room temperature for 15 minutes. A solution of 628.6 mg (2.74 mmol) of ethyl 6-chloronicotinate in 4 ml of dry tetrahydrofuran was transferred by double ended needle into a suspension of 380 mg (0.33 mmol) of tetrakistriphenylphosphine palladium in 5 ml dry tetrahydrofuran and mixture stirred at room temperature for 15 minutes and then treated by double ended needle with the solution of alkynylzinc prepared above. The mixture was stirred at room temperature for 20 hours and then quenched with ice and 30 ml of 3N hydrogen chloride. The mixture was extracted with 3×75 ml ether and ether extracts were combined and washed successively with saturated NaHCO$_3$ and saturated NaCl and then dried (MgSO$_4$). Solvent was removed in vacuo and the residue further purified by flash chromatography (silica; 10% ethyl acetate in hexane) to give the title compound as a yellow solid.

PMR (CDCl$_3$): δ1.36 (6H, s), 1.44 (3H, t, J~7.1 Hz), 1.83-1.87 (2H, m), 4.22-4.26 (2H, m), 4.44 (2H, q, J~7.1 Hz), 6.80 (1H, d, J~7.6 Hz), 7.35 (1H, d, J~8.9 Hz), 7.58 (1H, d, J~7.6 Hz), 7.60 (1H, M), 8.28 (1H, d, J~8.9 Hz), 9.21 (1H, s).

By this method, using the appropriate precursors, the following compounds are prepared:
ethyl 6-(2(4,4,7-trimethylchroman-6-yl)-ethynyl)nicotinate;
ethyl 6-(2-(4,4-dimethyl-7-ethylchroman-6-yl)ethynyl)nicotinate;
ethyl 6-(2-(4,4-dimethyl-7-propylchroman-6-yl)ethynyl)nicotinate;
ethyl 6-(2-(4,4-dimethyl-7-hexylchroman-6-yl)ethynyl)nicotinate;
ethyl (2-((4,4-dimethylchroman-6-yl)ethynyl)pyrid-5-yl)acetate;
ethyl (2-((4,4,7-trimethylchroman-6-yl)ethynyl)pyrid-5-yl)acetate;
ethyl (2-((4,4-dimethyl-7-ethylchroman-6-yl)ethynyl)pyrid-5-yl)acetate;
ethyl (2-((4,4-dimethyl-7-hexylchroman-6-yl)ethynyl)pyrid-5-yl)acetate;
ethyl 3-(2-((4,4-dimethylchroman-2-yl)ethynyl)pyrid-5-yl)propionate;
ethyl 3-(2-((4,4,7-trimethylchroman-6-yl)-ethynyl)pyrid-5-yl)propionate;
ethyl 3-(2((4,4-dimethyl-7-ethylchroman-6-yl)ethynyl)pyrid-5-yl)propionate;
ethyl 3-(2((4,4-dimethyl-7-hexylchroman-6-yl)ethynyl)pyrid-5-yl)propionate;
ethyl 5-(2-((4,4-dimethylchroman-6-yl)ethynyl)pyrid-5-yl)pentanoate;
ethyl 5-(2-((4,4,7-trimethylchroman-6-yl)ethynyl)pyrid-5-yl)pentanoate;
ethyl 5-(2-((4,4-dimethyl-7-ethylchroman-6-yl)ethynyl)pyrid-5-yl)pentanoate;
ethyl 5-(2-(4,4-dimethyl-7-hexylchroman-6-yl-ethynyl)pyrid-5-yl)pentanoate;
ethyl 5-(2-((4,4-dimethylchroman-6-yl)ethynyl)fur-2-yl)acetate;
ethyl (5-((4,4,7-trimethylchroman-6-yl)ethynyl)fur-2-yl)acetate;
ethyl (5-((4,4-dimethyl-7-ethylchroman-6-yl)ethynyl)fur-2-yl)acetate;
ethyl (5-((4,4-dimethyl-7-hexylchroman-6-yl)ethynyl)fur-2-yl)acetate;
ethyl 5-(5-((4,4-dimethylchroman-6-yl)ethynyl)fur-2-yl)pentanoate;
ethyl 5-(5-((4,4,7-trimethylchroman-6-yl)ethynyl)fur-2-yl)pentanoate;
ethyl 5-(5-((4,4-dimethyl-7-ethylchroman-6-yl)ethynyl)fur-2-yl)pentanoate;

ethyl 5-(5-((4,4-dimethyl-7-hexylchroman-6-yl)ethynyl)fur-2-yl)pentanoate;
ethyl (5-((4,4-dimethylchroman-6-yl)ethynyl)thien-2-yl)acetate;
ethyl (5-((4,4,7-trimethylchroman-6-yl)ethynyl)thien-2-yl)acetate;
ethyl (5-((4,4-dimethyl-7-ethylchroman-6-yl)ethynyl)-thien-2-yl)acetate;
ethyl (5-((4,4-dimethyl-7-hexylchroman-6-yl)ethynyl)-thien-2-yl)acetate;
ethyl 5-(5-((4,4-dimethylchroman-6-yl)ethynyl)thien-2-yl)pentanoate;
ethyl 5-(5-((4,4,7-trimethylchroman-6-yl)-ethynyl)thien-2-yl)pentanoate;
ethyl 5-(5-((4,4-dimethyl-7-ethylchroman-6-yl)ethynyl)-thien-2-yl)pentanoate;
ethyl 5-(5-((4,4-dimethyl-7-hexylchroman-6-yl)ethynyl)thien-2-yl)pentanoate;
ethyl (6-((4,4-dimethylchroman-6-yl)ethynyl)pyridazin-3-yl)acetate;
ethyl (6-((4,4,7-trimethylchroman-6-yl)ethynyl)pyridazin-3-yl)acetate;
ethyl (6-((4,4-dimethyl-7-ethylchroman-6-yl)ethynyl)-pyridazin-3-yl)acetate;
ethyl (6-((4,4-dimethyl-7-hexylchroman-6-yl)ethynyl)-pyridazin-3-yl)acetate;
ethyl 5-(6-((4,4-dimethylchroman-6-yl)ethynyl)pyridazin-3-yl)pentanoate;
ethyl 5-(6-((4,4,7-trimethylchroman-6-yl)-ethynyl)-pyridazin-3-yl)pentanoate;
ethyl 5-(6-((4,4-dimethyl-7-ethylchroman-6-yl)ethynyl)-pyridazin-3-yl)pentanoate;
ethyl 5-(6-((4,4-dimethyl-7-hexylchroman-6-yl)ethynyl)pyridazin-3-yl)pentanoate;
ethyl (5-((4,4-dimethylchroman-6-yl)ethynyl)pyrimidin-2-yl)acetate;
ethyl (5-((4,4,7-trimethylchroman-6-yl)ethynyl)pyrimidin-2-yl)acetate;
ethyl (5-((4,4-dimethyl-7-ethylchroman-6-yl)ethynyl)-pyrimidin-2-yl)acetate;
ethyl (5-((4,4-dimethyl-7-hexylchroman-6-yl)ethynyl)-pyrimidin-2-yl)acetate;
ethyl 5-(5-((4,4-dimethylchroman-6-yl)ethynyl)pyrimidin-2-yl)pentanoate;
ethyl 5-(5-((4,4,7-trimethylchroman-6-yl)-ethynyl)-pyrimidin-2-yl)pentanoate;
ethyl 5-(5-((4,4-dimethyl-7-ethylchroman-6-yl)ethynyl)-pyrimidin-2-yl)pentanoate;
ethyl 5-(5-((4,4-dimethyl-7-hexylchroman-6-yl)ethynyl)pyrimidin-2-yl)pentanoate;
ethyl (5-((4,4-dimethylchroman-6-yl)ethynyl)pyrazin-2-yl)acetate;
ethyl (5-((4,4,7-trimethylchroman-6-yl)ethynyl)pyrazin-2-yl)acetate;
ethyl (5-((4,4-dimethyl-7-ethylchroman-6-yl)ethynyl)-pyrazin-2-yl)acetate;
ethyl (5-((4,4-dimethyl-7-hexylchroman-6-yl)ethynyl)-pyrazin-2-yl)acetate;
ethyl 5)(5-((4,4-dimethylchroman-6-yl)ethynyl)pyrazin-2-yl)pentanoate;
ethyl 5-(5-((4,4,7-trimethylchroman-6-yl)-ethynyl)pyrazin-2-yl)pentanoate;
ethyl 5-(5-((4,4-dimethyl-7-ethylchroman-6-yl)ethynyl)-pyrazin-2-yl)pentanoate; and
ethyl 5-(5-((4,4-dimethyl-7-hexylchroman-6-yl)ethynyl)pyrazin-2-yl)pentanoate.

EXAMPLE 19

N-(4-Bromophenyl)-3,3-dimethylacrylamide

To a solution of 9.48 g (80 mmol) of 3,3-dimethylacryloyl chloride in 200 ml of dry tetrahydrofuran (THF) was added with vigorous shaking a solution of 13.76 g (80 mmol) of 4-bromoaniline in 300 ml of dry THF. The mixture stood at room temperature for 2 hours and was then treated with 80 g of ice followed by 200 ml of hexane. The organic layer was separated and the aqueous layer was extracted with 2×50 ml of hexanes. The organic layers were combined and washed successively with 30 ml of water and 2×30 ml of saturated NaCl solution and then dried ($MgSO_4$). The solvent was removed in vacuo and the residue purified by recrystallization from an ethyl acetate and hexanes mixture to give the title compound as colorless crystals.

PMR ($CDCl_3$): $\delta$1.91 (3H, s), 2.23 (3H, s), 5.73 (1H, broad s), 7.38-7.55 (5H, m).

EXAMPLE 20

4,4-Dimethyl-6-bromo-2-oxo-1,2,3,4-tetrahydroquinoline

To 6.7 g (26.02 mmol) of molten N-(4-bromophenyl)3,3-dimethylacrylamide (heated to 135° C.) was added 4.15 g (31.09) of aluminum chloride over 25 minutes. The reaction mixture was stirred at 130° C. for 16 hopurs and then treated with a further 1 g of aluminum chloride. The reaction mixture was heated at 130° C. for a further 9 hours and then cooled to room temperature. The reaction was then quenched by the slow addition of 100 ml of ice cold water with slight warming of flask to facilitate mixing. The mixture was extracted with 1×100 ml and 4×50 ml of ether. The organic extracts were combined and washed with 25 ml of saturated NaCl solution and then dried ($MgSO_4$). The solvent was removed in vacuo and the residue purified by flash chromatography (silica; 30% ethyl acetate in hexanes) to give the title compound as a pale yellow solid.

PMR ($CDCl_3$): $\delta$1.37 (6H, s), 2.53 (2H, s), 6.85 (1H, d, J~8.4 Hz), 7.32 (1H, dd, J~8.4 Hz, 2.1 Hz), 7.43 (1H, d, J~2.1 Hz), 10.12 (1H, broad s).

EXAMPLE 21

4,4-Dimethyl-6-bromo-1,2,3,4-tetrahydroquinoline

To 23.5 ml of 1.0M (23.5 mmol) lithium aluminum hydride in THF, heated to reflux under nitrogen, was added a solution of 4.95 g (19.48 mmol) of 4,4-dimethyl-6-bromo-2-oxo-1,2,3,4-tetrahydroquinoline in 50 ml of dry THF and 100 ml of dry diethyl ether via a double-ended needle. The mixture was heated at a reflux for 2 hours and then cooled to room temperature. The reaction mixture was then quenched by the slow addition of 25 ml of water followed by 50 ml of 5% NaOH solution. The mixture was extracted with 2×25 ml of ether, the organic extracts were combined and washed successively with 25 ml each of water and saturated NaCl solution and then dried ($MgSO_4$). The solvent was removed in vacuo and the residue purified by flash chromatography (silica; 15% ethyl acetate in hexanes) to give the title compound as a brown oil.

PMR ($CDCl_3$): $\delta$1.27 (6H, s), 1.67-1.74 (2H, m), 3.23-3.32 (2H, m), 3.90 (1H, broad s), 6.33 (1H, d, J~8.4 Hz), 7.10 (1H, dd, J~8.4 Hz, 2.3 Hz), 7.25 (1H, d, J~2.3 Hz).

EXAMPLE 22

4,4-Dimethyl-6-trimethylsilylethynyl-1,2,3,4-tetrahydroquinoline

A solution of 1.608 g (6.7 mmol) of 4,4-dimethyl-6-bromo-1,2,3,4-tetrahydroquinoline in 1.5 ml of triethylamine in a heavy-walled tube was degassed under argon and then treated with 75 mg (0.39 mmol) of cuprous iodide and 150 mg (0.21 mmol) of bis(triphenylphosphine) palladium (II) chloride. The mixture was degassed again under argon, treated with 2.09 g (21.2 mmol) of trimethylsilylacetylene and the tube was sealed. The mixture was heated at 50° C. for 48 hours. After cooling to room temperature methylene chloride was added to the reaction mixture and the mixture filtered. The filtrate was concentrated in vacuo and the residue purified by flash chromatography (silica; 10% ethyl acetate in hexanes) to give the title compound as a yellow oil.

PMR (CDCl$_3$): $\delta$0.20 (9H, s), 1.20 (6H, s), 1.57–1.63 (2H, m), 3.16–3.25 (2H, m), 4.02 (1H, broad s), 6.24 (1H, d, J~8.2 Hz), 7.00 (1H, dd, J~8.2 Hz, 1.8 Hz), 7.26 (1H, d, J~1.8 Hz).

EXAMPLE 23

4,4-Dimethyl-6-ethynyl-1,2,3,4-tetrahydroquinoline

To a solution of 569 mg (2.21 mmol) of 4,4-dimethyl-6-trimethylsilylethynyl-1,2,3,4-tetrahydroquinoline in 3 ml of isopropanol was added, under argon, 1 ml of 1N aqueous KOH solution. The reaction mixture was stirred at room temperature for 36 hours and the isopropanol was removed under vacuum. The residue was extracted with ether and the ether extract was washed successively with water and saturated NaCl solution and then dried (MgSO$_4$). The solvent was removed in vacuo and the residue was purified by flash chromatography (silica; 10% ethyl acetate in hexanes) to give the title compound as a brown oil.

PMR (CDCl$_3$): $\delta$1.26 (6H, s), 1.65–1.72 (2H, m), 2.96 (1H, s), 3.27–3.34 (2H, m), 6.34 (1H, d, J~8.3 Hz), 7.08 (1H, dd, J~8.3 Hz, 1.6 Hz), 7.33 (1H, d, J~1.6 Hz).

EXAMPLE 24

6-(2-(4,4-dimethylchroman-6-yl)ethynyl)nicotinic acid

The absolute ethanol used in this experiment was degassed by applying a vacuum while simultaneously bubbling nitrogen through it. A solution of 101.1 mg (0.30 mmol) of ethyl 6-(2-4,4-dimethylchroman-6-yl)ethylyl)-nicotinoate in 2 ml ethanol was treated under argon with 0.7 ml of a 1.81M (1.27 mmol) solution of potassium hydroxide in ethanol and water. This mixture was stirred at room temperature for 60 hours and then solvent removed in vacuo. The residue was dissolved in 25 ml of water and extracted with 25 ml of ether. The aqueous layer was acidified with glacial acetic acid and extracted with 4×50 ml of ether. Ether extracts were combined and washed with water, then saturated NaCl and dried (MgSO$_4$). Solvent was then removed in vacuo to give the title compound. PMR ((CD$_3$)$_2$CO): $\delta$1.40 (6H, s) 1.88–1.92 (2H, m), 4.26–4.30 (2H, m), 6.82 (1H, d, J~8.7 Hz), 7.37 (1H, dd, J~7.6 Hz, 2.2 Hz), 7.62 (1H, M), 7.63 (1H, d, J~8.7 Hz), 8.37 (1H, dd, J~7.6 Hz, 2.2 Hz), 9.27 (1H, d, J~2.2 Hz).

Proceeding in the same manner 6-(2-(4,4-dimethylthiochroman-6-yl)ethynyl)nicotinic acid was prepared from ethyl 6-(2-(4,4-dimethylthiochroman-6-yl)-ethynyl)nicotinoate.

PMR (CDCl$_3$(CD$_3$)$_2$CO): $\delta$1.37 (6H, M), 1.99 (2H, m), 3.09 (2H, m), 7.10 (1H, d, J~8.1 Hz), 7.28 (1H, dd, J~8.1 Hz), 2.1 Hz), 7.64 (1H, dd, J~7.8 Hz), 1.8 Hz), 7.65 (1H, d, J~7.8 Hz, 1.5 Hz), 9.24 (1H, m).

Proceeding in the same manner, the esters prepared as per the preceeding Examples may be converted to their corresponding acid.

EXAMPLE 25

6-(2-(4,4-Dimethyl-thiochroman-6-yl)-ethynyl)-3-pyridylmethanol

To 3.0 ml of 1M lithium aluminum hydride (3.0 mmol) in THF, cooled to −78° C., was added dropwise over 5 min a solution of 2.0 g (5.9 mmol) of ethyl 6-(2-(4,4-dimethylthiochroman-6-yl)-ethynyl)nicotinate in 5 ml of THF. The reaction mixture was stirred at −78° C. for 40 min and then treated with 2 ml of water. The mixture was warmed to room temperature and the organic layer was separated. The aqueous layer was extracted with 3×10 ml of ether. The organic extracts were combined and washed successively with 1×10 ml of dilute HCl, 3×10 ml of water and 1×15 ml of saturated NaCl solution and then dried (MgSO$_4$). The solvent was removed in vacuo and the residue purified by flash chromatography (silica; 50% ethyl acetate in hexanes) to give the title compound as a pale yellow solid.

PMR (CDCl$_3$): $\delta$1.33 (6H, s), 1.91–1.98 (2H, m), 3.01–3.07 (2H, m), 4.75 (2H, s), 7.08 (1H, d, J~8.2 Hz), 7.23 (1H, dd, J~8.2 Hz, 1.7 Hz), 7.46 (1H, d, J~7.9 Hz), 7.60 (1H, d, J~1.2 Hz), 7.71 (1H, dd, J~7.9 Hz, 1.2 Hz), 8.51 (1H, broad s).

EXAMPLE 26

2-(4,4-dimethyl-thiochroman-6-yl)ethynyl)-5-bromopyridine

A mixture of 6.36 g (31.5 mmol) of 4,4-dimethyl-6-ethynylthiochroman, 7.46 g (31.5 mmol) of 2,5-dibromopyridine, 122 mg (0.64 mmol) of cuprous iodide, 224 mg (0.32 mmol) of bis(triphenylphosphine) palladium (II) chloride and 70 ml of freshly distilled triethylamine was degassed under nitrogen and stirred at room temperature for 1 hour. The mixture was then treated with 180 ml of ether and 40 ml of water and the organic layer was separated. The aqueous layer was extracted with ether, the organic layers were combined and then washed with 2×40 ml of water, 2×40 ml of saturated NaCl solution and then dried (K$_2$CO$_3$). The solvent was removed in vacuo and the residue purified by flash chromatography (silica; 5% ethyl acetate in hexanes) and recrystallization from ethyl acetate and hexane to give the title compound as a pale brown solid.

PMR (CDCl$_3$): $\delta$1.34 (6H, s), 1.94–1.98 (2H, m), 3.04–3.08 (2H, m), 7.08 (1H, d, J~8.4 Hz), 7.23 (1H, dd, J~8.4 Hz, 1.8 Hz), 7.38 (1H, J~8.4 Hz), 7.60 (1H, d, J~1.8 Hz), 7.78 (1H, dd, J~8.4, 2.3 Hz), 8.66 (1H, d, J~2.3 Hz).

EXAMPLE 27

2-(2-(4,4-dimethylthiochroman-6-yl)-ethynyl)-5-pyridinecarboxaldehyde

To a cooled (−78° C.) solution of 358 mg (1.0 mmol) of 2-(4,4-dimethylthiochroman-6-yl)ethynyl-5-bromopyridine in 5 ml of anhydrous ether was added slowly under nitrogen 1.3 ml of 1.7M (2.21 mmol) tertbutyl lithium in pentane. The mixture was stirred at −78° C. for 1 h and then treated with 95 mg (1.3 mmol) of anhydrous dimethylformamide. The mixture was stirred at −78° C. for a further 0.5 hours, then warmed to 0° C. and treated with 5 ml of saturated NH$_4$Cl solution followed by 5 ml of ether. The organic layer was separated and the aqueous layer was extracted with ether. The organic layers were combined, washed successively with water and saturated NaCl solution and then dried (MgSO$_4$). The solvent was then removed in vacuo and the residue purified by flash chromatography (silica; 15% ethyl acetate in hexanes) followed by high pressure liquid chromatography (Whatman M-9 Partisil 10/50 column, 15% ethyl acetate in hexanes) to give the title compound as a pale yellow solid.

PMR (CDCl$_3$): δ1.33 (6H, s), 1.93–1.97 (2H, m), 3.03–3.07 (2H, m), 7.08 (1H, d, J∼8.2 Hz), 7.26 (1H, dd, J∼8.2 Hz, 1.8 Hz), 7.63–7.65 (2H, m), 8.14 (2H, dd, J∼8.0 Hz, 2.3 Hz) 9.05 (1H, d, J∼2.3 Hz), 10.1 (1H, s).

EXAMPLE 28

2-[2-(4,4-Dimethylchroman-6-yl)ethynyl]-5-hydroxymethylpyridine

A 250 ml 3-necked flask is fitted with a stirrer, a dropping funnel, a nitrogen inlet and a thermometer. In the flask is placed a solution of 379.5 mg (10 mmol) of lithium aluminum hydride in 30 ml of dry diethyl ether. The solution is cooled to −65° C. under nitrogen and a solution of 3.2343 g (10 mmol) of ethyl 6-[2-(4,4-dimethylchroman-6-yl)ethylyl]nicotinate in 15 ml of dry ether is added dropwise at a rate such that the temperature does not exceed −60° C. The mixture is stirred at −30° C. for 1 hour and the excess hydride is then destroyed by the addition of 300 mg (3.4 mmol) of ethyl acetate. The reaction mixture is then hydrolyzed by adding 3 ml of saturated ammonium chloride solution and allowing the temperature to rise to room temperature. The mixture is then filtered and the residue washed with ether. The ether layer is then washed with saturated sodium chloride solution, dried (MgSO$_4$) and then concentrated in vacuo. The residue is purified by chromatography followed by recrystallization to give the title compound.

By the same process, acids or esters of this invention may be converted to their corresponding primary alcohol.

EXAMPLE 29

2-[2-(4,4-Dimethylchroman-6-yl)ethynyl]-5-acetoxymethylpyridine

A solution of 2.81 g (10 mmol) of 2-[2-(4,4-dimethylchroman-6-yl)ethynyl]-5-hydromymethylpyridine, 600 mg (10 mmol) of glacial acetic acid, 2.06 g (10 mmol) of dicyclohexylcarbodiimide and 460 mg (3.765 mmol) of 4-dimethylaminopyridine in 150 ml methylene chloride is stirred at room temperature for 48 hours. The reaction mixture is then filtered and the residue washed with 50 ml of methylene chloride. The filtrate is then concentrated in vacuo and the residue is purified by chromatography followed by recrystallization to give the title compound.

Proceeding in the same manner, other alcohols of this invention may be esterified.

EXAMPLE 30

2-(2-(4,4-Dimethylchroman-6-yl)ethynyl)pyridine-5-carboxaldehyde

A solution of 1.396 g (11 mmol) of freshly distilled oxalyl chloride in 25 ml of methylene chloride is placed in a 4-necked flask equipped with a stirrer, a thermometer and two pressure-equalizing addition funnels fitted with drying tubes. The solution is cooled to −60° C. and then treated dropwise with a solution of 1.875 g (24 mmol) of dimethyl sulfoxide (distilled from calcium hydride) in 5 ml of methylene chloride over a five minute period. The reaction mixture is then stirred at −60° C. for an additional 10 minutes. A solution of 2.82 g (10 mmol) of 2-[2-(4,4-dimethylchroman-6-yl)ethynyl]-5-hydromymethylpyridine in 10 ml of methylene chloride is then added to the reaction mixture over a period of 5 minutes. The mixture is stirred for a further 15 minutes and is then treated with 5.06 g (50 mmol) of triethylamine. The cooling bath is then removed and the mixture is allowed to warm to room temperature. Thirty ml of water is then added to the mixture and stirring is continued for a further 10 minutes. The organic layer is then separated and the aqueous layer is extracted with 20 ml of methylene chloride. The organic layers are then combined and washed successively with dilute HCl, water and dilute Na$_2$CO$_3$ solution and then dried (MgSO$_4$). The solution is then filtered and concentrated in vacuo and the residue is purified by chromatography followed by recrystallization to give the title compound.

Primary alcohols of this invention may be oxidized to their corresponding aldehyde by this method.

EXAMPLE 31

2-(2-(4,4-Dimethylchroman-6-yl)ethynyl)-5-(1-hydroxypropyl)pyridine

Four ml of a 3M (12 mmol) solution of ethylmagnesium bromide in ether is placed in a 3-necked flask fitted with a mechanical stirrer, a reflux condenser protected by a drying tube and a pressure-equalizing dropping funnel protected by a drying tube. The flask is cooled in an ice bath and a solution of 2.8 g (10 mmol) of 2-(2-(4,4-Dimethylchroman-6-yl)ethynyl)pyridine-5-carboxaldehyde in 10 ml of dry ether is added slowly with vigorous stirring. The cooling bath is then removed and the mixture heated at reflux for 3 hours. The mixture is then cooled in an ice-salt bath and 5 ml of saturated ammonium chloride solution added. The mixture is stirred for a further 1 hour and then filtered and the residue washed with two 10 ml portions of ether. The ether solution is then separated, dried (MgSO$_4$) and the ether removed in vacuo. The residue is then purified by chromatography followed by recrystallization to give the title compound.

Using the same procedure any of the other aldehydes of this invention can be converted to a secondary alcohol.

Such secondary alcohols may be converted to their corresponding ketone using the procedure recited in Example 15.

EXAMPLE 32

2-(2-(4,4-Dimethylchroman-6-yl)ethynyl)-5-dimethoxymethylpyridine

A round-bottomed flask is fitted with a Dean-Stark apparatus under a reflux condenser protected by a drying tube. A mixture of 3.35 g (12 mmol) of 2-(4,4-dimethylchroman-6-yl)ethynyl)-pyridine-5-carboxaldehyde, 4.80 mg (15 mmol) of anhydrous methanol, 2 mg of P-toluenesulfonic acid monohydrate and 10 ml of anhydrous benzene is placed in the flask and the mixture heated at reflux under nitrogen until close to the theoretical amount of water is collected in the Dean-Stark trap. The reaction mixture is cooled to room temperature and extracted successively with 5 ml of 10% sodium hydroxide solution and two 5 ml portions of water and then dried (MgSO$_4$). The solution is then filtered and the solvent removed in vacuo. The residue is purified by chromatography and then recrystallization to give the title compound.

In a similar manner, any aldehyde or ketone of this invention may be converted to an acetal or a ketal.

EXAMPLE 33

Preferably, these compounds may be administered topically using various formulations. Such formulation may be as follows:

| Ingredient | Weight/Percent |
| --- | --- |
| Solution | |
| Retinoid | 0.1 |
| BHT 0.1 | |
| Alcohol USP | 58.0 |
| Polyethylene Glycol 400 NF | 41.8 |
| Gel | |
| Retinoid | 0.1 |
| BHT 0.1 | |
| Alcohol USP | 97.8 |
| Hydroxypropyl Cellulose | 2.0 |

What is claimed is:

1. A compound of the formula

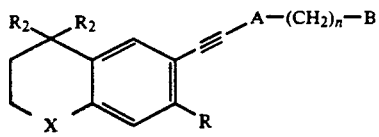

where X is S or O; R is hydrogen or lower alkyl; R$_2$ is methyl; A is pyridyl; n is 0–2; and B is H, —COOH or a pharmaceutically acceptable salt thereof, or an ester thereof with a saturated aliphatic alcohol of ten or fewer carbon atoms, or with a cyclic or saturated aliphatic cyclic alcohol of 5 to 10 carbon atoms, or with phenol or with a lower alkylphenol, or an amide or a mono or disubstituted amide thereof, the substituents on the amide being selected from a group consisting of saturated aliphatic radicals of ten or fewer carbon atoms, cyclic or saturated aliphatic cyclic radicals of 5 to 10 carbon atoms, and phenyl or lower alkylphenyl radicals, or B is CH$_2$OH or an ester derivative thereof derived from a saturated aliphatic acid of ten or fewer carbon atoms, or from a cyclic or saturated aliphatic cyclic acid of 5 to 10 carbon atoms, or from benzoic acid, or an ether derivative thereof derived from a saturated aliphatic radical of ten or fewer carbon atoms, or from a cyclic or saturated aliphatic cyclic radical of 5 to 10 carbon atoms, or from phenyl or lower alkylphenyl radical, or B is —CHO or a lower alkyl acetal derivative thereof, or an acetal derivative thereof formed with a lower alkyl diol, or B is —COR$_1$ or a lower alkyl ketal derivative thereof, or a ketal derivative thereof formed with a lower alkyl diol, where R$_1$ is —(CH$_2$)$_m$CH$_3$ where m is 0–4, or a pharmaceutically acceptable salt of the compound defined in said formula.

2. A compound of claim 1 where X is S, R is hydrogen, and n is 0 or 1.

3. A compound of claim 2 where B is —COOH or a pharmaceutically acceptable salt, lower alkyl ester or mono- or di-lower alkyl amide thereof.

4. Ethyl 6-(2-(4,4-dimethylthiochroman-6-yl)ethynyl)nicotinate.

5. 6-(2-(4,4-dimethylthiochroman-6-yl)ethynyl)nicotinic acid or a pharmaceutically acceptable salt thereof.

6. A compound of the formula

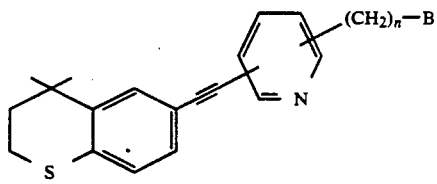

where n is 0 or 1 and where B is —CH$_2$OH or a lower alkyl ether or lower alkyl acid ester thereof.

7. A compound of claim 6 which is 6-(2-(4,4-dimethylthiochroman-6-yl)-ethynyl)-3-pyridylmethanol.

8. A compound of claim 2 where B is —CHO or an acetal derivative thereof.

9. A compound of claim 8 which is 2-(2-(4,4-dimethylthiochroman-6-yl)-ethynyl)-5-pyridinecarboxaldehyde.

10. A compound of the formula

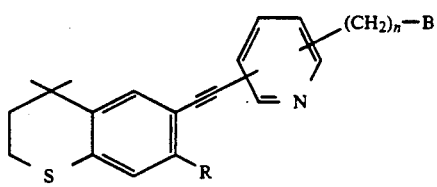

where R is lower alkyl, n is 0 or 1, and B is H, —COOH or a pharmaceutically acceptable salt thereof, or an ester thereof with a saturated aliphatic alcohol of ten or fewer carbon atoms, or with a cyclic or saturated aliphatic cyclic alcohol of 5 to 10 carbon atoms, or with phenol or with a lower alkylphenol, or an amide or a mono or di-substituted amide thereof, the substituents on the amide being selected from a group consisting of saturated aliphatic radicals of ten or fewer carbon atoms, cyclic or saturated aliphatic cyclic radicals of 5 to 10 carbon atoms, and phenyl or lower alkylphenyl radicals, or B is CH$_2$OH or an ester derivative thereof derived from a saturated aliphatic acid of ten or fewer carbon atoms, or from a cyclic or saturated aliphatic cyclic acid of 5 to 10 carbon atoms, or from benzoic acid, or an ether derivative thereof derived from a saturated aliphatic radical of ten or fewer carbon atoms, or from a cyclic or saturated aliphatic cyclic radical of 5 to 10 carbon atoms, or from phenyl or lower alkylphenyl radical, or B is —CHO or a lower alkyl acetal derivative thereof, or an acetal derivative thereof formed with a lower alkyl diol, or B is —COR₁ or a lower alkyl ketal derivative thereof, or a ketal derivative thereof formed with a lower alkyl diol, where $R_1$ is —(CH$_2$)$_m$CH$_3$ where m is 0–4, or a pharmaceutically acceptable salt of the compound defined in said formula.

11. A compound of claim 10 which is 6-(2-(4,4,7-trimethylthiochroman-6-yl)ethynyl)nicotinic acid or a pharmaceutically acceptable salt thereof.

12. A compound of the formula

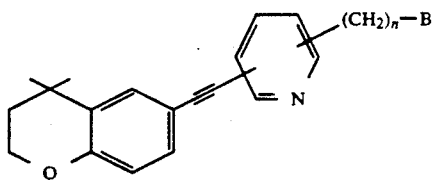

where n is 0 or 1, and B is H, —COOH or a pharmaceutically acceptable salt thereof, or an ester thereof with a saturated aliphatic alcohol of ten or fewer carbon atoms, or with a cyclic or saturated aliphatic cyclic alcohol of 5 to 10 carbon atoms, or with phenol or with a lower alkylphenol, or an amide or a mono or di-substituted amide thereof, the subtituents on the amide being selected from a group consisting of saturated aliphatic radicals of ten or fewer carbon atoms, cyclic or saturated aliphatic cyclic radicals of 5 to 10 carbon atoms, and phenyl or lower alkylphenyl radicals, or B is CH₂OH or an ester derivative thereof derived from a saturated aliphatic acid of ten or fewer carbon atoms, or from a cyclic or saturated aliphatic cyclic acid of 5 to 10 carbon atoms, or from benzoic acid, or an ether derivative thereof derived from a saturated aliphatic radical of ten or fewer carbon atoms, or from a cyclic or saturated aliphatic cyclic radical of 5 to 10 carbon atoms, or from phenyl or lower alkylphenyl radical, or B is —CHO or a lower alkyl acetal derivative thereof, or an acetal derivative thereof formed with a lower alkyl diol, or B is —COR₁ or a lower alkyl ketal derivative thereof, or a ketal derivative thereof formed with a lower alkyl diol, where $R_1$ is —(CH$_2$)$_m$CH$_3$ where m is 0–4, or a pharmaceutically acceptable salt of the compound defined in said formula.

13. A compound of claim 12 where B is —COOH or a pharmaceutically acceptable salt, lower alkyl ester or mono- or di-lower alkyl amide thereof.

14. 6-(2-(4,4-dimethylchroman-6-yl)ethynyl)nicotinic acid or a pharmaceutically acceptable salt thereof.

15. Ethyl 6-(2-(4,4-dimethylchroman-6-yl)ethynyl)-nicotinate.

16. A compound of claim 12 where B is —CH₂OH or a lower alkyl ether or lower alkyl acid ester thereof.

17. A compound of claim 12 where B is —CHO or an acetal derivative thereof.

18. A pharmaceutical composition comprising a pharmaceutically acceptable excipient and a compound of the formula

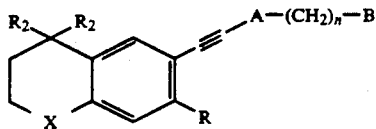

where X is S or O; R is hydrogen or lower alkyl; R₂ is methyl; A is pyridyl; n is 0–2; and B is H, —COOH or a pharmaceutically acceptable salt thereof, or an ester thereof with a saturated aliphatic alcohol of ten or fewer carbon atoms, or with a cyclic or saturated aliphatic cyclic alcohol of 5 to 10 carbon atoms, or with phenol or with a lower alkylphenol, or an amide or a mono or di-substituted amide thereof, the subtituents on the amide being selected from a group consisting of saturated aliphatic radicals of ten or fewer carbon atoms, cyclic or saturated aliphatic cyclic radicals of 5 to 10 carbon atoms, and phenyl or lower alkylphenyl radicals, or B is CH₂OH or an ester derivative thereof derived from a saturated aliphatic acid of ten or fewer carbon atoms, or from a cyclic or saturated aliphatic cyclic acid of 5 to 10 carbon atoms, or from benzoic acid, or an ether derivative thereof derived from a saturated aliphatic radical of ten or fewer carbon atoms, or from a cyclic or saturated aliphatic cyclic radical of 5 to 10 carbon atoms, or from phenyl or lower alkylphenyl radical, or B is —CHO or a lower alkyl acetal derivative thereof, or an acetal derivative thereof formed with a lower alkyl diol, or B is —COR₁ or a lower alkyl ketal derivative thereof, or a ketal derivative thereof formed with a lower alkyl diol, where $R_1$ is —(CH$_2$)$_m$CH$_3$ where m is 0–4, or a pharmaceutically acceptable salt of the compound defined in said formula.

19. A method of treating psoriasis in a mammal which method comprises administering alone or in conjunction with a pharmaceutically acceptable excipient, a therapeutically effective amount of a compound of the formula

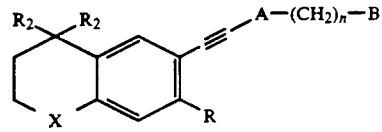

where X is S or O; R is hydrogen or lower alkyl; R₂ is methyl; A is pyridyl; n is 0–2; and B is H, —COOH or a pharmaceutically acceptable salt thereof, or an ester thereof with a saturated aliphatic alcohol of ten or fewer carbon atoms, or with a cyclic or saturated aliphatic cyclic alcohol of 5 to 10 carbon atoms, or with phenol or with a lower alkylphenol, or an amide or a mono or di-substituted amide thereof, the subtituents on the amide being selected from a group consisting of saturated aliphatic radicals of ten or fewer carbon atoms, cyclic or saturated aliphatic cyclic radicals of 5 to 10 carbon atoms, and phenyl or lower alkylphenyl radicals, or B is CH₂OH or an ester derivative thereof derived from a saturated aliphatic acid of ten or fewer carbon atoms, or from a cyclic or saturated aliphatic cyclic acid of 5 to 10 carbon atoms, or from benzoic acid, or an ether derivative thereof derived from a saturated aliphatic radical of ten or fewer carbon atoms, or from a cyclic or saturated aliphatic cyclic radical of 5 to 10 carbon atoms, or from phenyl or lower alkylphenyl radical, or B is —CHO or a lower alkyl acetal derivative thereof, or an acetal derivative thereof formed with a lower alkyl diol, or B is —COR₁ or a lower alkyl ketal derivative thereof, or a ketal derivative thereof formed with a lower alkyl diol, where $R_1$ is —(CH$_2$)$_m$CH$_3$ where m is 0–4, or a pharmaceutically acceptable salt of the compound defined in said formula.

* * * * *

UNITED STATES PATENT AND TRADEMARK OFFICE
CERTIFICATE OF CORRECTION

PATENT NO. : 5,089,509
DATED : February 18, 1992
INVENTOR(S) : Roshantha A.S. Chandraratna It is certified that error appears in the above-indentified patent and that said Letters Patent is hereby corrected as shown below:

Column 3, line 18, before "amine" add —or an—;
Column 19, line 48, "prazin" should be —pyrazin—.

Signed and Sealed this

Twenty-first Day of June, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,089,509
DATED : February 18, 1992
INVENTOR(S) : Roshantha A. S. Chandraratna It is certified that error appears in the above-indentified patent and that said Letters Patent is hereby corrected as shown below:

Column 17, line 64, "mgSO$_4$" should be --MgSO$_4$--;

Column 19, line 45, "5)5" should be --5(5--;

Column 26, line 30, "hopurs" should be --hours--;

Column 34, line 28, "of" should be --for--.

Signed and Sealed this

Eleventh Day of October, 1994

Attest:

BRUCE LEHMAN

Attesting Officer  Commissioner of Patents and Trademarks

UNITED STATES PATENT AND TRADEMARK OFFICE

CERTIFICATE EXTENDING PATENT TERM
UNDER 35 U.S.C. § 156

| | | |
|---|---|---|
| PATENT NO. | : | 5,089,509 |
| ISSUED | : | February 18, 1992 |
| INVENTOR | : | Roshantha A. S. Chandraratna |
| PATENT OWNER | : | Allergan, Inc. |
| PRODUCT | : | TAZORAC® (tazarotene) |

This is to certify that an application under 35 U.S.C. § 156 has been filed in the U.S. Patent and Trademark Office, requesting extension of the term of U.S. Patent No. 5,089,509 based upon the regulatory review of the product TAZORAC® (tazarotene) by the Food and Drug Administration. Since it appears that the requirements of the law have been met, this certificate extends the term of the patent for the period of 845 days from February 18, 2009, the original expiration date of the patent, subject to the provisions of 35 U.S.C. § 41(b), with all rights pertaining thereto as provided by 35 U.S.C. § 156(b).

I have caused the seal of the U.S. Patent and Trademark Office to be affixed this 12th day of September 2000.

Q. Todd Dickinson
Under Secretary of Commerce for Intellectual Property and Director of the United States Patent and Trademark Office